(12) United States Patent
Li et al.

(10) Patent No.: US 6,376,687 B1
(45) Date of Patent: *Apr. 23, 2002

(54) STEROID SULFATASE INHIBITORS AND METHODS FOR MAKING AND USING THE SAME

(75) Inventors: Pui-Kai Li, Galloway, OH (US); Chikara Murakata; Shiro Akinaga, both of Shizuoka-Ken (JP)

(73) Assignees: Duquesne University of the Holy Ghost, Pittsburgh, PA (US); Kyowa Hakko Kogyo Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/490,302

(22) Filed: Jan. 24, 2000

Related U.S. Application Data

(63) Continuation-in-part of application No. 09/236,842, filed on Jan. 25, 1999, now Pat. No. 6,288,050, which is a continuation-in-part of application No. 08/897,247, filed on Jul. 18, 1997, now Pat. No. 5,880,115.

(51) Int. Cl.$^7$ .................................................. C07J 3/00
(52) U.S. Cl. ...................................................... 552/611
(58) Field of Search ......................................... 552/611

(56) References Cited

U.S. PATENT DOCUMENTS

| | | | |
|---|---|---|---|
| 5,556,847 A | 9/1996 | Johnson et al. | |
| 5,567,831 A | 10/1996 | Li | |
| 5,571,933 A | 11/1996 | Li et al. | |
| 5,604,215 A | 2/1997 | Reed et al. | |
| 5,616,574 A | 4/1997 | Reed et al. | |
| 5,763,432 A | 6/1998 | Tanabe et al. | |
| 5,763,492 A | 6/1998 | Johnson et al. | |
| 5,880,115 A | * 3/1999 | Li et al. ..................... | 514/169 |

FOREIGN PATENT DOCUMENTS

| | | |
|---|---|---|
| DE | 86393 | 12/1971 |
| WO | WO 98/32763 | 7/1998 |
| WO | WO 99/33858 | 7/1999 |

OTHER PUBLICATIONS

Howarth et al., "Phosphonates and Thiophosphonates As Sulfate Surrogates: Synthesis of Estrone 3–Methylthiophosphonate, A Potent Inhibitor of Estrone Sulfatase", *Bioorg. Med. Chem. Lett.*, vol. 3, pp. 313–318 (1993).

Duncan et al., "Inhibition of Estrone Sulfatase Activity by Estrone–3–methylthiophosphonate: A Potential Therapeutic Agent in Breast Cancer", *Cancer Res.*, vol. 53, pp. 298–302 (Jan. 15, 1993).

Li et al., "Synthesis and biochemical studies of estrone sulfatase inhibitors", *Steroids*, vol. 58, pp. 106–111 (Mar. 1993).

Dibbelt et al., "Inhibition of Human Placental Sterylsulfatase by Synthetic Analogs of Estrone Sulfate", *J. Steroid Biochem. Molec. Biol.*, vol. 50, No. 5/6, pp. 261–266 (1994).

Howarth, et al., "Estrone Sulfamates: Potent Inhibitors of Estrone Sulfatase with Therapeutic Potential", *J. Med. Chem.*, vol. 37, pp. 219–221 (1994).

Purohit et al., In Vivo Inhibition of Oestrone Sulphatase and Dehydroepiandrosterone Sulphatase By Oestrone–3–0–Sulphamate, *Int. H. Cancer*, vol. 63, pp. 106–111 (1995).

Li et al., "Estrone sulfate analogs as estrone sulfatase inhibitors", *Steroids*, vol. 60, pp. 299–306 (1995).

Selcer, et al., "Inhibition of Placental Estrone Sulfatase Activity and MCF–7 Breast Cancer Cell Proliferation by Estrone–3–amino Derivatives", *J. Steroid Biochem. Molec. Biol.*, vol. 59, No. 1, pp. 83–91 (1996).

\* cited by examiner

*Primary Examiner*—Barbara P. Badio
(74) *Attorney, Agent, or Firm*—Debra Z. Anderson; Diane R. Meyers; Eckert Seamans Cherin & Mellott, LLC

(57) ABSTRACT

Novel sulfatase inhibitor compounds useful in the treatment of estrogen dependent illnesses are disclosed. These compounds generally comprise a steroid nucleus substituted at the C17 position. Methods for synthesizing these compounds and using them in the therapeutic and/or prophylactic treatment of a patient are also disclosed.

9 Claims, 12 Drawing Sheets

STEROID SULFATASE INHIBITORS AND METHODS FOR MAKING AND USING THE SAME

CROSS-REFERENCE TO RELATED APPLICATION

This is a continuation-in-part of U.S. Ser. No. 09/236,842, filed on Jan. 25, 1999 now U.S. Pat. No. 6,288,056, which is a continuation-in-part of U.S. Ser. No. 08/897,274, filed on Jul. 18, 1997 now U.S. Pat. No. 5,880,115.

FIELD OF THE INVENTION

The present invention relates to sulfatase inhibitors and methods for making and using the same. These methods include use of these compounds in therapeutic and prophylactic treatments for estrogen dependent illnesses.

BACKGROUND OF THE INVENTION

Estrogen levels in breast tumors of post-menopausal women are at least ten times higher than estrogen levels in plasma. The high levels of estrogen in these tumors are due to in situ formation of estrogen, possibly through conversion of estrone sulfate to estrone by the enzyme estrone sulfatase. Inhibitors of estrone sulfatase are therefore potential agents for the treatment of estrogen-dependent breast cancers. Most estrone sulfatase inhibitors are steroidal in nature. Although estrone-3-O-sulfamate (EMATE) is believed to be the most potent inhibitor of estrone sulfatase, recent evidence indicates that this compound is a potent estrogen. This compound is therefore not useful in the treatment of estrogen dependent illnesses.

Reed and co-workers reported on sulfatase inhibitory activities of estrone-3-O-methylthiophosphonate, estrone-3-O alkyl and aryl sulfonates, estrone-3-O-phosphonates and thiophosphonates and estrone sulfamates in: Duncan et al., "Inhibition of Estrone Sulfatase Activity by Estrone-3-methylthiophosphonate", *Cancer Res.* 53:298–303 (1993); Howarth et al., "Phosphonates and Thiophosphonates as Sulfate Surrogates: Synthesis of Estrone-3-methylthiophosphonate, a Potent Inhibitor of Estrone Sulfatase", *Bioorg. Med. Chem. Lett.* 3:313–318 (1993); Howarth et al., "Estrone Sulfamates: Potent Inhibitors of Estrone Sulfatase with Therapeutic Potential", *J. Med. Chem.* 37:219–221 (1994); and Purohit et al., "!In vivo Inhibition of Oestrone Sulphatase and Dehydroepiandrosterone Sulphatase by Oestrone-3-O-sulphamate", *Int. J. Cancer*, 63:106–111 (1995).

Li and co-workers reported the synthesis and sulfatase inhibitory activities of sulfonate and its analogues, methylene sulfonates and phosphate that contain the estrone nucleus in Li et al., "Synthesis and Biochemical Studies of Estrone Sulfatase Inhibitors", *Steroids*, 58:106–111 (1993); Dibbelt et al., "Inhibition of Human Placental Sterylsulfatase by Synthetic Analogs of Estrone Sulfate", *J. Steroid Biochem. Molec. Biol.*, 50(5/6):261–266 (1994); and Li et al., "Estrone Sulfate Analogs as Estrone Sulfatase Inhibitors", *Steroids* 60:299–306 (1995).

Estrone-3-amino derivatives are reported in Selcer et al., "Inhibition of Placental Estrone Sulfatase Activity and MCF-7 Breast Cancer Cell Proliferation by Estrone-3-amino Derivatives", *J. Steroid Biochem. Molec. Biol.*, 59(1):83–91 (1996).

U.S. Pat. No. 5,567,831 is directed to the use of non-steroidal sulfatase inhibitor compounds in the treatment of estrogen dependent illnesses.

U.S. Pat. No. 5,571,933 is directed to derivatives of estra 1,3,5(10)trien-17-one, 3-amino compounds and methods for using these compounds in the treatment of estrogen dependent illnesses.

U.S. Pat. Nos. 5,556,847 and 5,763,492, are directed to steroidal and non-steroidal sulfatase inhibitors, respectively, and methods for using these inhibitors to effect memory enhancement. Use of these inhibitors in the treatment of estrogen dependent illnesses is not disclosed.

U.S. Pat. Nos. 5,616,574 and 5,604,215 disclose steroid sulphatase inhibitors and the methods of using the same. The disclosed compounds are potent estrogens and metabolize to form estrones, in contrast to the compounds of the present invention.

U.S. Pat. No. 5,763,432 discloses steroid inhibitors of estrone sulfatase; the patent does not appear to disclose the compounds of the present invention, or compounds in which the substituent at the C17 position of a steroid nucleus interacts with a lipid bilayer.

There remains a need for potent sulfatase inhibitors that are metabolically stable, more selective, and devoid of estrogenic activity.

SUMMARY OF THE INVENTION

The present invention has met the above described need by providing non-estrogenic compounds useful as steroid sulfatase inhibitors. These compounds generally comprise a substituted steroid ring system having 4 attached rings; in the compounds of the present invention this structure is generally depicted by formula 1:

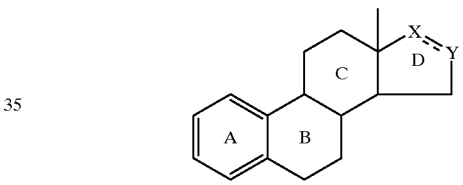

wherein X and Y are both carbons and the bond between X and Y is either single or double, as is further described below. The compounds of the present invention can be generally described as sulfatase inhibitors, and derive this inhibition ability from the presence of an

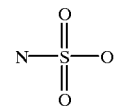

group. The nitrogen in this group can be further substituted with one or more hydrogen atoms, one or more lower alkyl groups having 1 to 6 carbons, or combinations thereof. Thus, the present compounds comprise a sulfamate group or a 6-membered cyclic sulfamate group attached to the "A" ring of the steroid nucleus, thereby resulting in a compound with 5 attached rings. More specifically, the group can be attached to the "A" ring in the steroid nucleus in which case a sulfamate ester of the steroid would be represented. Alternatively, the "N", "S", and the "O" attached to the S by a single bond can, together with a carbon attached to the N, form a fifth ring adjacent to the "A" ring of the steroid nucleus. The bond between the N and the carbon could be double, in which case an oxathiazine dioxide would be represented, or single, in which case a dihydro-oxathiazine dioxide ring would be represented.

The present invention is also directed to methods for synthesizing the steroid sulfatase inhibitors disclosed herein.

In addition, the present invention relates to methods for using these compounds as sulfatase inhibitors. These methods generally comprise incorporating one or more of the compounds into a suitable pharmaceutical carrier and administering a therapeutically or prophylactically effective amount of the compound to a patient.

It is an aspect of this invention to provide compounds for inhibiting the steroid sulfatase enzyme produced in the body.

It is a further aspect of the invention to provide estrone sulfatase inhibitor compounds having anti-tumor or synergistic activity with anti-estrogen and aromatase inhibitors.

It is a further aspect of the present invention to provide estrone sulfatase inhibitor compounds having activity against estrogen dependent illnesses.

Yet another aspect of the invention is to provide methods for therapeutically or prophylactically treating a patient with the sulfatase inhibitor compounds of the present invention.

It is another aspect of this invention to provide derivatives of sulfatase inhibitor compounds that are not metabolized to compounds that are estrogenic.

These and other aspects of the invention will be more fully understood to those skilled in the art upon review of the following description and appended claims.

DETAILED DESCRIPTION OF THE INVENTION

Figure 1:
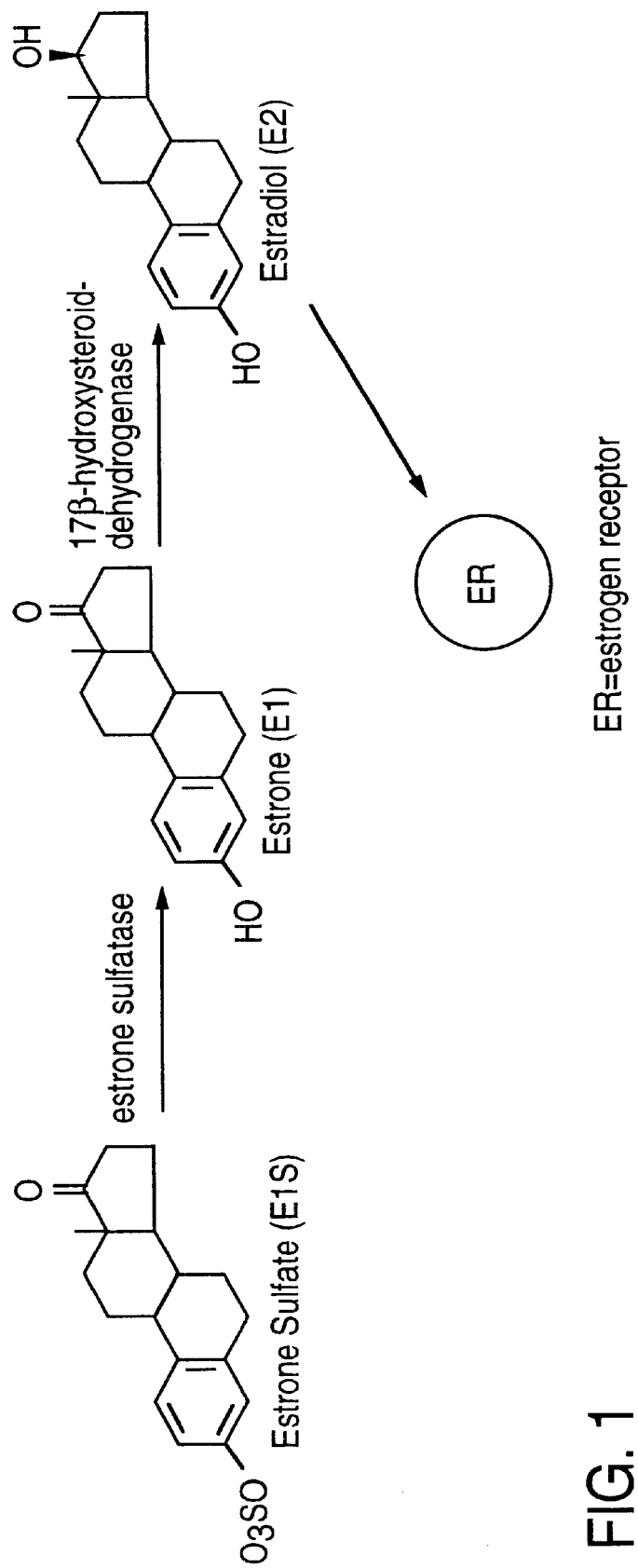
FIG. 1 generally illustrates the estrone sulfatase pathway.

As used herein, the term "patient" refers to members of the animal kingdom including but not limited to human beings.

The present invention is directed to compounds having formula 2:

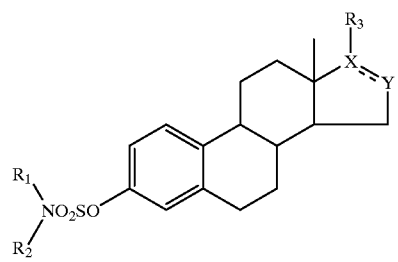

wherein $R_1$ and $R_2$ are independently selected from hydrogen and a lower alkyl group having one to six carbons;

$R_3$ is selected from the group:

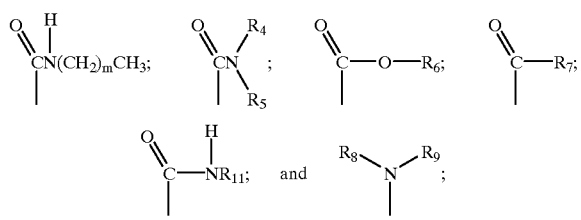

$R_4$ and $R_5$ are independently selected from hydrogen, straight or branched chain alkyl groups having one to fourteen carbons, and straight or branched chain alkoxy groups having one to six carbons;

$R_6$ is selected from hydrogen and straight or branched chain alkyl groups having one to fourteen carbons;

$R_7$ is selected from

hydrogen and straight or branched chain alkyl groups having one to fourteen carbons, $R_2$ and $R_{13}$ are independently selected from hydrogen, straight or branched chain alkyl groups having one to fourteen carbons and straight or branched chain alkoxy groups having one to six carbons, and $R_{14}$ is selected from hydrogen, and straight or branched chain alkyl groups having one to fourteen carbons;

$R_8$ is selected from hydrogen and straight or branched chain alkyl groups having one to six carbons;

$R_9$ is selected from straight or branched chain alkanoyl groups having one to fifteen carbons, straight or branched chain alkyl groups having one to fourteen carbons, $CO(CH_2)_mCH_3$ and $COR_{10}$;

$R_{10}$ is a straight or branched chain alkyl group having one to fourteen carbons, but the alkyl group is not a branched chain when the alkyl group is a $C_1$ or $C_2$ alkyl group;

m is 0 to 2;

$R_{11}$ is a branched chain alkyl group having three to fourteen carbons; and

X and Y are both carbons and the bond between X and Y is either single or double, except when $R_3$ is

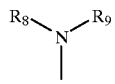

the bond between X and Y is single.

As will be appreciated by those skilled in the art, these compounds are estrones, more particularly 1,3,5(10) trienes. Suitable steroid ring systems include the substituted estrones:

2-OH-estrone
2-methoxy-estrone
4-OH-estrone
6 alpha-OH-estrone
7 alpha-OH-estrone
7 alpha-alkylamido-estrone
16 alpha-OH-estrone
16 beta-OH-estrone The present invention is further directed to compounds having the formula (3):

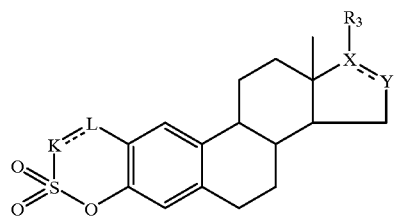

wherein $R_3$ is selected from

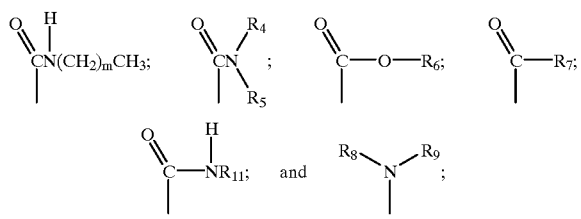

$R_4$ and $R_5$ are independently selected from hydrogen, straight or branched chain alkyl groups having one to fourteen carbons, and straight or branched chain alkoxy groups having one to six carbons;

$R_6$ is selected from hydrogen and straight or branched chain alkyl groups having one to fourteen carbons;

$R_7$ is selected from

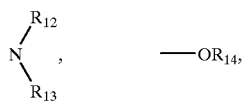

hydrogen and straight or branched chain alkyl groups having one to fourteen carbons, $R_{12}$ and $R_{13}$ are independently selected from hydrogen, straight or branched chain alkyl groups having one to fourteen carbons and straight or branched chain alkoxy groups having one to six carbons, and $R_{14}$ is selected from hydrogen, and straight or branched chain alkyl groups having one to fourteen carbons;

$R_8$ is selected from hydrogen and straight or branched chain alkyl groups having one to six carbons;

$R_9$ is selected from straight or branched chain alkanoyl groups having one to fifteen carbons, straight or branched chain alkyl groups having one to fourteen carbons, $CO(CH_2)_mCH_3$ and $COR_{10}$;

$R_{10}$ is a straight or branched chain alkyl group having one to fourteen carbons, but the alkyl group is not a branched chain when the alkyl group is a $C_1$ or $C_2$ alkyl group;

m is 0 to 2;

$R_{11}$ is a branched chain alkyl group having three to fourteen carbons;

X and Y are both carbons and the bond between X and Y is either single or double, except when $R_3$ is

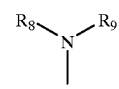

the bond between X and Y is single; and

K is nitrogen and L is carbon and the bond between K and L is either single or double.

For the compounds represented by Formulas 2 and 3, "X", "Y" and "L" are all carbon, and "K" is nitrogen; the bond connecting X and Y, and K and L can generally be either a single bond or a double bond. It will be appreciated that when the bond is single, the X and K have a hydrogen attached thereto, and the Y and L have two hydrogens attached thereto.

Numerous estrones are therefore the subject of the present invention. For ease of reference, these compounds, which generally have either formula 2 or formula 3 as described above, will be referred to herein as Class 1 through Class 12 compounds depending on the "$R_3$" attachment, as identified in Table 1 below: Class 1 through Class 6 refer to compounds of formula 2 and Class 7 through Class 12 refer to compounds of formula 3.

TABLE 1

| Class for Formula 2 | Class for Formula 3 | $R_3$ |
|---|---|---|
| Class 1 | Class 7 | 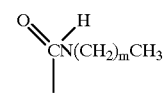 |
| Class 2 | Class 8 | 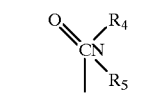 |
| Class 3 | Class 9 | 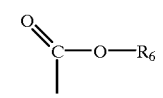 |
| Class 4 | Class 10 | 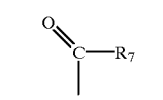 |

TABLE 1-continued

| Class for Formula 2 | Class for Formula 3 | $R_3$ |
|---|---|---|
| Class 5 | Class 11 | 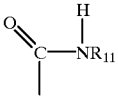 |
| Class 6 | Class 12 |  |

Preferably, $R_1$ and $R_2$ are both hydrogen. Further preferred embodiments include compounds of Classes 1 and 7 wherein m is equal to 2; compounds of Classes 2 and 8 wherein $R_4$ and $R_5$ are both $CH_3$; compounds of Classes 2 and 8 wherein $R_4$ is hydrogen and $R_5$ is a straight or branched chain alkyl group having one to eight carbons or a straight or branched chain alkoxy group having one to three carbons; compounds of Classes 2 and 8 wherein $R_4$ is a straight or branched chain alkyl group having one to five carbons and $R_5$ is a straight or branched chain alkyl group having one to six carbons; compounds of Classes 3 and 9 wherein $R_6$ is a straight or branched chain alkyl group having one to eight carbons, especially $CH_2CH_3$; compounds of Classes 4 and 10 wherein $R_7$ is a straight or branched chain alkyl group having one to eight carbons, especially a straight chain alkyl group having three carbons (propyl); compounds of Classes 4 and 10 wherein $R_7$ is

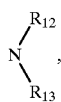

$R_{12}$ and $R_{13}$ are both hydrogen, methyl, propyl or isopropyl; or $R_{12}$ is ethyl and $R_{13}$ is isopropyl; compounds of Classes 5 and 11 wherein $R_{11}$ is a straight or branched chain alkyl group having three to eight carbons, especially a branched chain alkyl group having three carbons (isopropyl); compounds of Classes 6 and 12 wherein $R_8$ is hydrogen or a straight or branched chain alkyl group having one to six carbons and $R_9$ is a straight or branched chain alkyl group having two to eight carbons or a straight or branched chain alkanoyl group having one to eight carbons; and compounds of Classes 6 and 12 wherein $R_8$ is hydrogen and $R_9$ is a straight or branched chain alkanoyl having four carbons.

The compounds of the present invention are useful as sulfatase inhibitors. These compounds generally include a substituted steroid nucleus. The substituent is attached to the steroid nucleus at the C17 position of the nucleus. This is represented in Formulas 2 and 3 as the "$R_3$" group. Because of the unique substituents found at the C17 position of the steroid nucleus in the present compounds, the steroidal molecule released after inactivation of the enzyme is not estrogenic. The compounds of the present invention function as active-site directed irreversible inhibitors of estrone sulfatase. The sulfamate group recognizes and binds to the steroid sulfatase or estrone sulfatase in the estrone sulfatase pathway, thereby preventing the conversion of estrone sulfate to estrone. The estrone sulfatase pathway is shown in FIG. 1.

Figure 2:
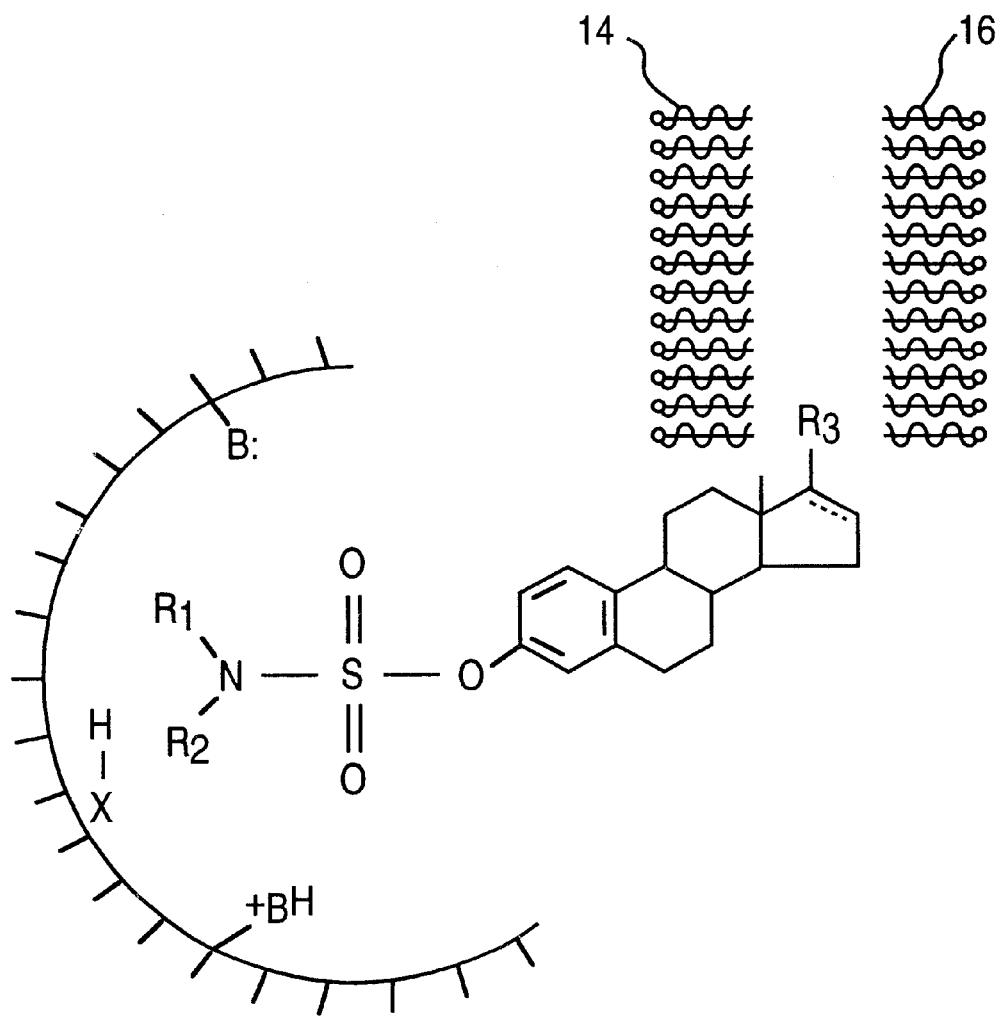
FIG. 2 illustrates the manner in which a C17 substituent, represented by "$R_3$" in the Figure, interacts with a lipid bilayer.

In addition, the unique substituents at the C17 position of the steroid nucleus provide enhanced sulfatase inhibition when compared to compounds lacking these substituents. Since estrone sulfatase is a membrane bound enzyme, the substituents on the C17 position as described herein provide for a hydrophobic interaction between the substituent and the lipid bilayers of various membranes of the patient. This interaction results in an increase in the binding affinity of the inhibitor to the enzyme. As illustrated in FIG. 2, the C17 substituent ($R_3$) interacts with the two layers (14 and 16) of the lipid bilayer of a membrane. Hydrophobic interaction keeps the substituent within the bilayer. This additional binding site results in more potent sulfatase inhibitory activity.

The present invention is further directed to the synthesis of the above-described compounds. Various reaction schemes are illustrated in FIGS. 3–12.

Figure 3:
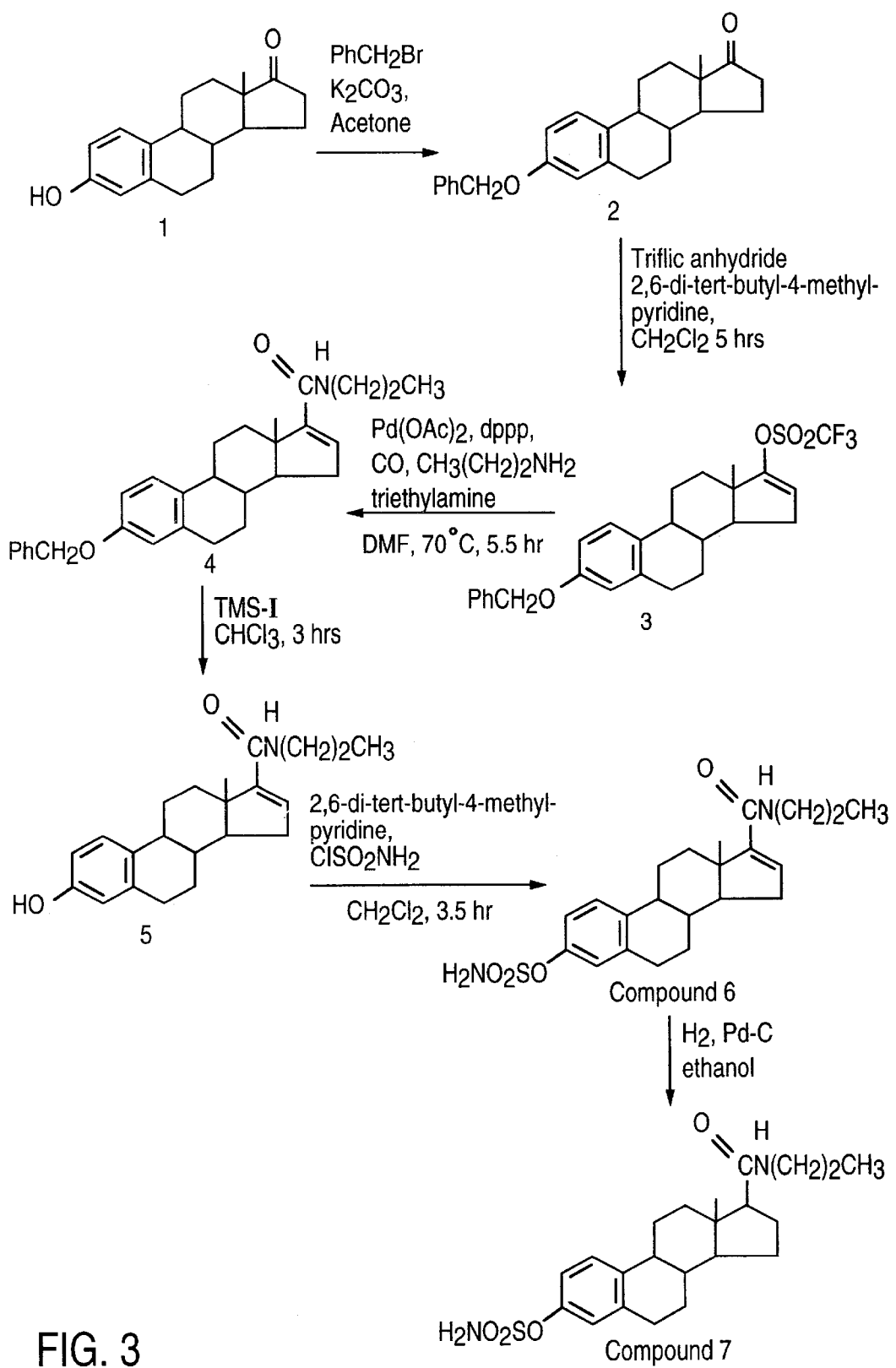
FIG. 3 illustrates a scheme for preparing a compound of Class 1, according to the methods of Example 1.

FIG. 3 outlines the synthesis of a compound of formula 2 when $R_1$ and $R_2$ are both equal to hydrogen and $R_3$ equals

Figure 4:
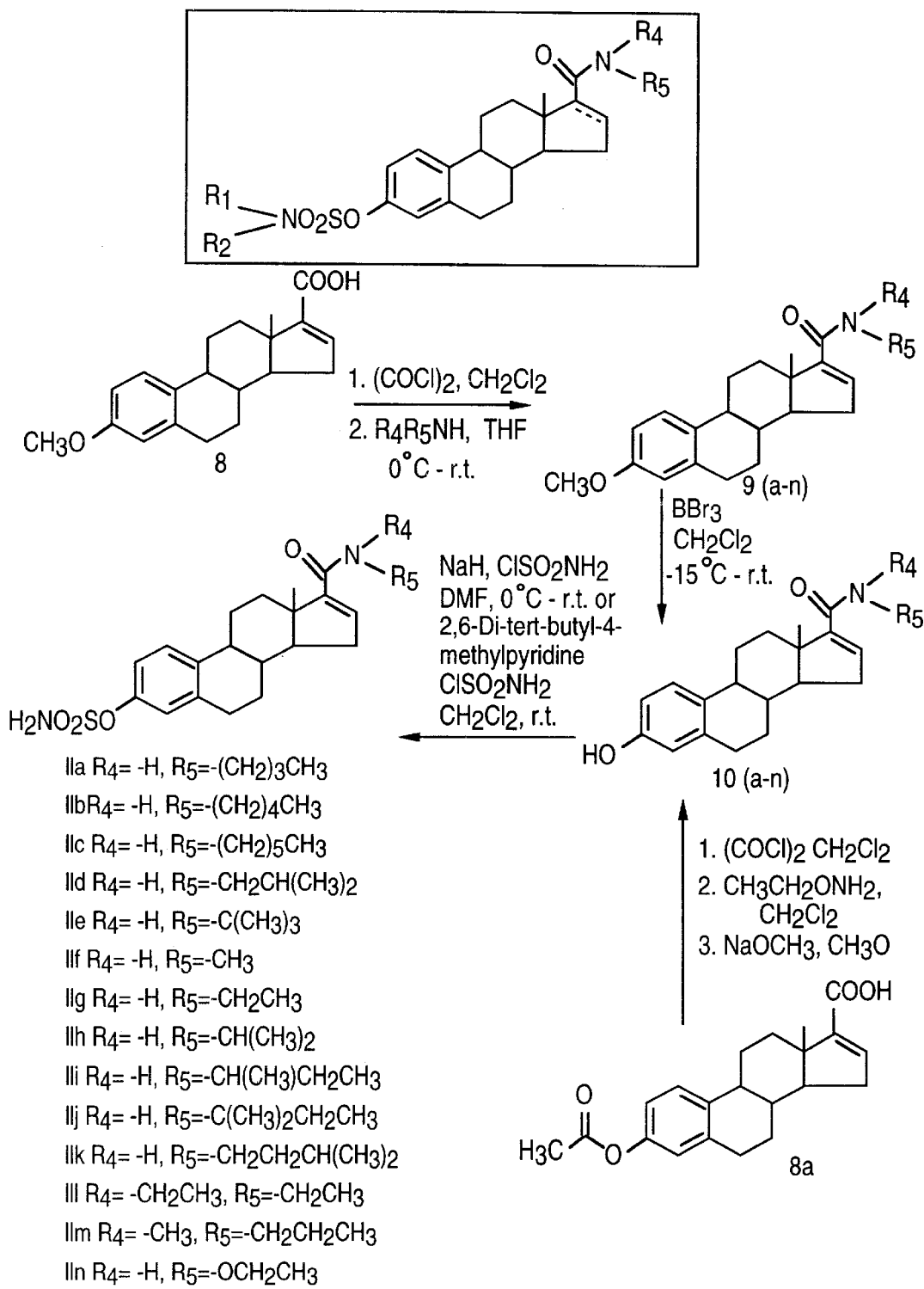
FIG. 4 illustrates a scheme for preparing compounds of Class 2, according to the methods of Example 2.
Figure 5:
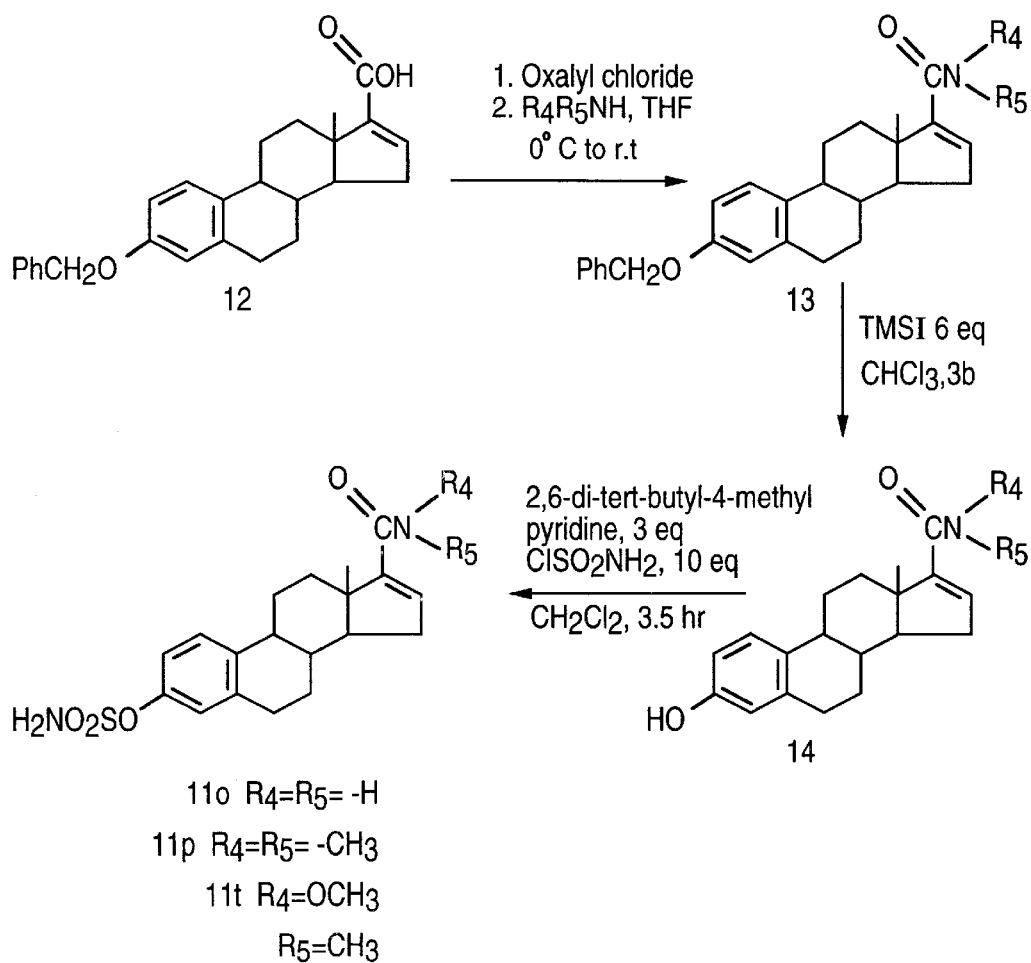
FIG. 5 illustrates a scheme for preparing compounds of Class 2, according to the methods of Example 2.
Figure 6:
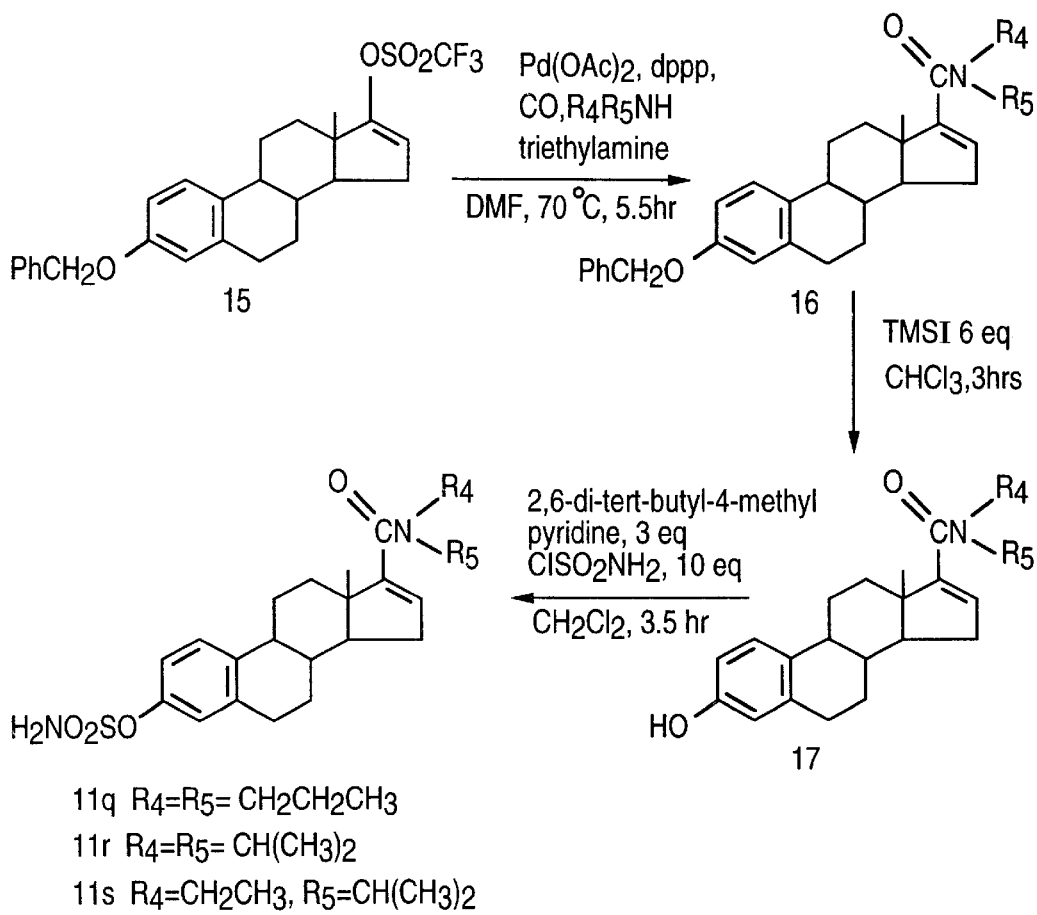
FIG. 6 illustrates a scheme for preparing compounds of Class 2, according to the methods of Example 2.

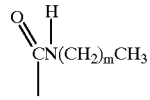

with m equal to 2. This is a compound of Class 1. FIGS. 4, 5 and 6 illustrate the synthesis of compounds of Class 2. The particular compounds synthesized in FIG. 4 are generally represented by formula 2 wherein $R_1$ and $R_2$ are both hydrogen, $R_3$ is

and $R_4$ is hydrogen, methyl, ethyl, propyl or isopropyl and $R_5$ is any of the "$R_5$" groups corresponding with compounds 11a–11s in FIGS. 4, 5 and 6.

Figure 7:
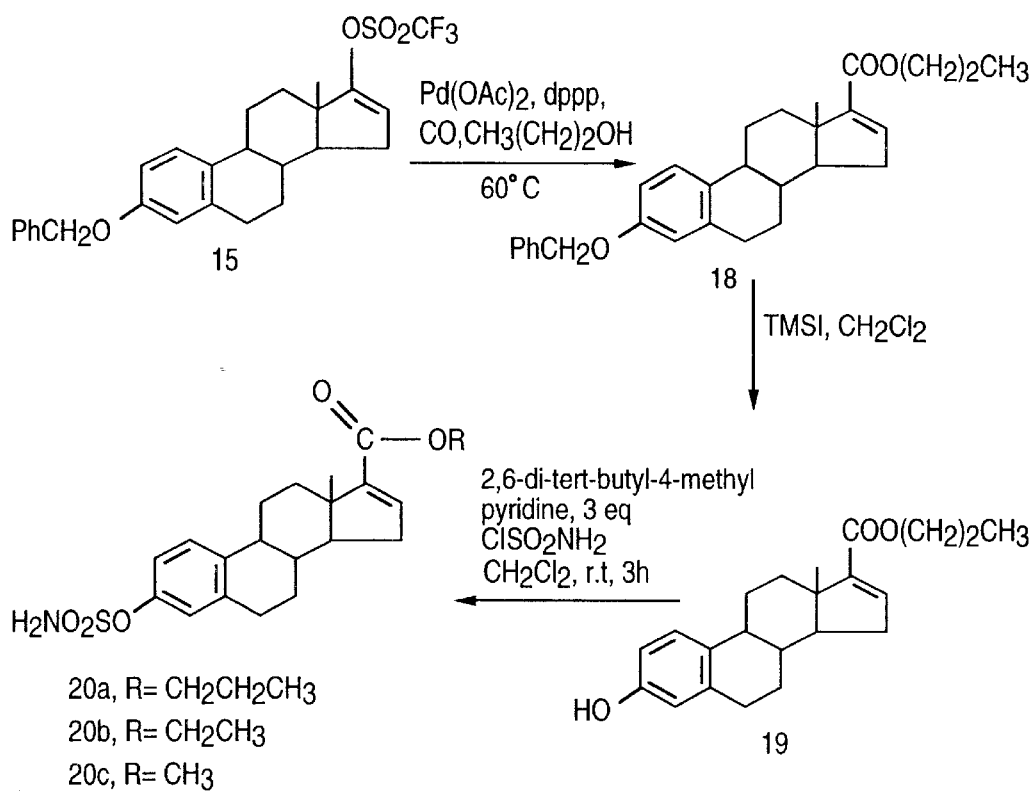
FIG. 7 illustrates a scheme for preparing a compound of Class 3, according to the methods of Example 3.

FIG. 7 shows a method of synthesizing a compound of Class 3, which is generally represented by formula 2 above, wherein $R_3$ is

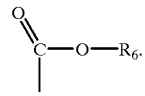

Figure 8:
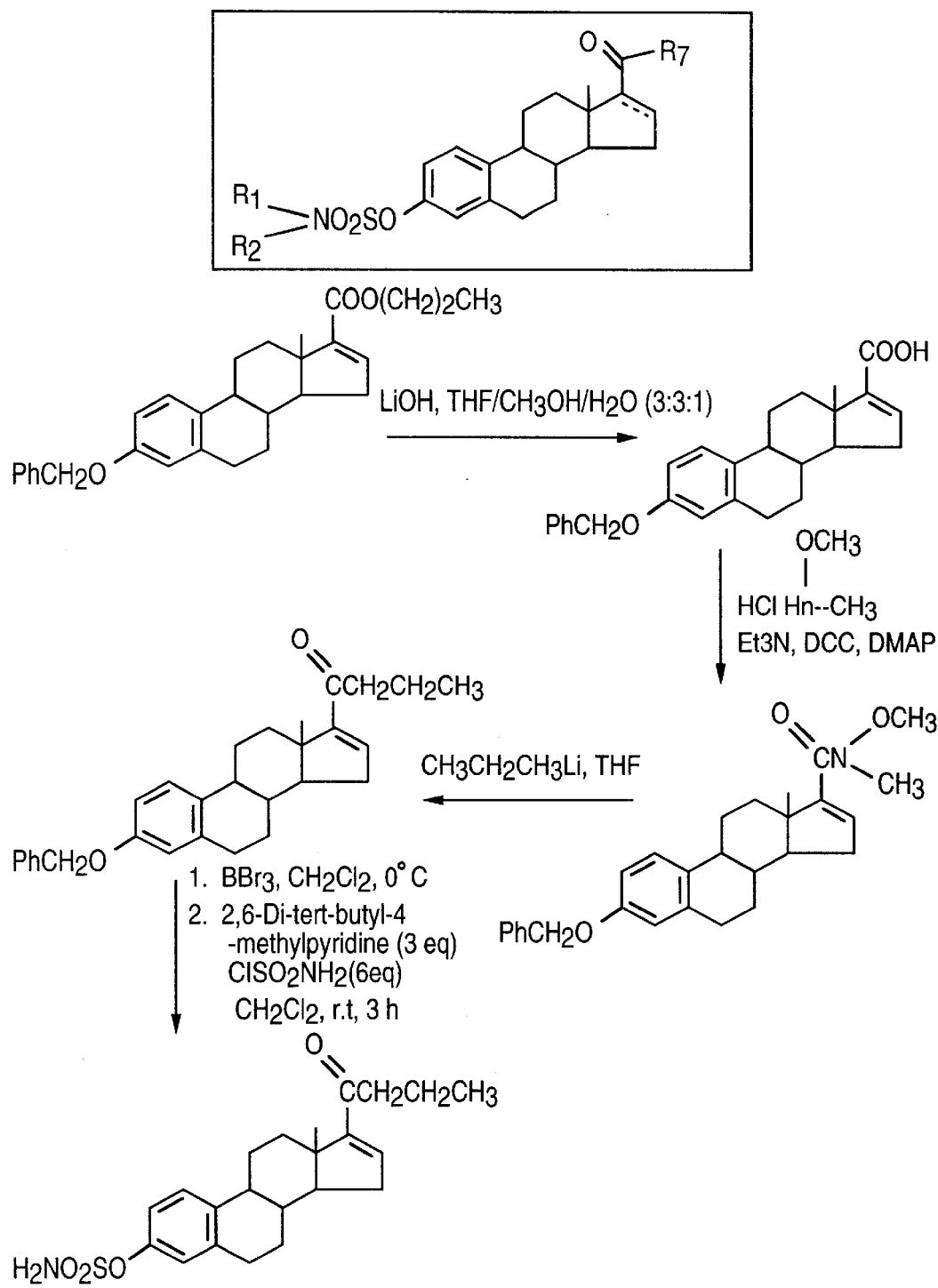
FIG. 8 illustrates a scheme for preparing a compound of Class 4.

The particular embodiment of the Class 3 compound shown in FIG. 7 is represented by formula 2 wherein $R_1$ and $R_2$ are both hydrogen and $R_6$ is a straight chain alkyl group having 3 carbons. FIG. 8 depicts the synthesis of a compound of Class 4, generally represented by formula 2 above wherein $R_3$ equals

The particular embodiment of the Class 3 compound shown in FIG. 8 represents formula 2 wherein $R_1$ and $R_2$ are both hydrogen and $R_7$ is a straight chain alkyl group having 3 carbons. It will be understood by those skilled in the art that the Figures depict specific embodiments of the various compounds generally represented by formula 2; other compounds within formula 2 having different "R" groups or different "m" values can easily be prepared by those skilled in the art by following the schemes generally outlined in the Figures and making the necessary substitutions.

Figure 9:
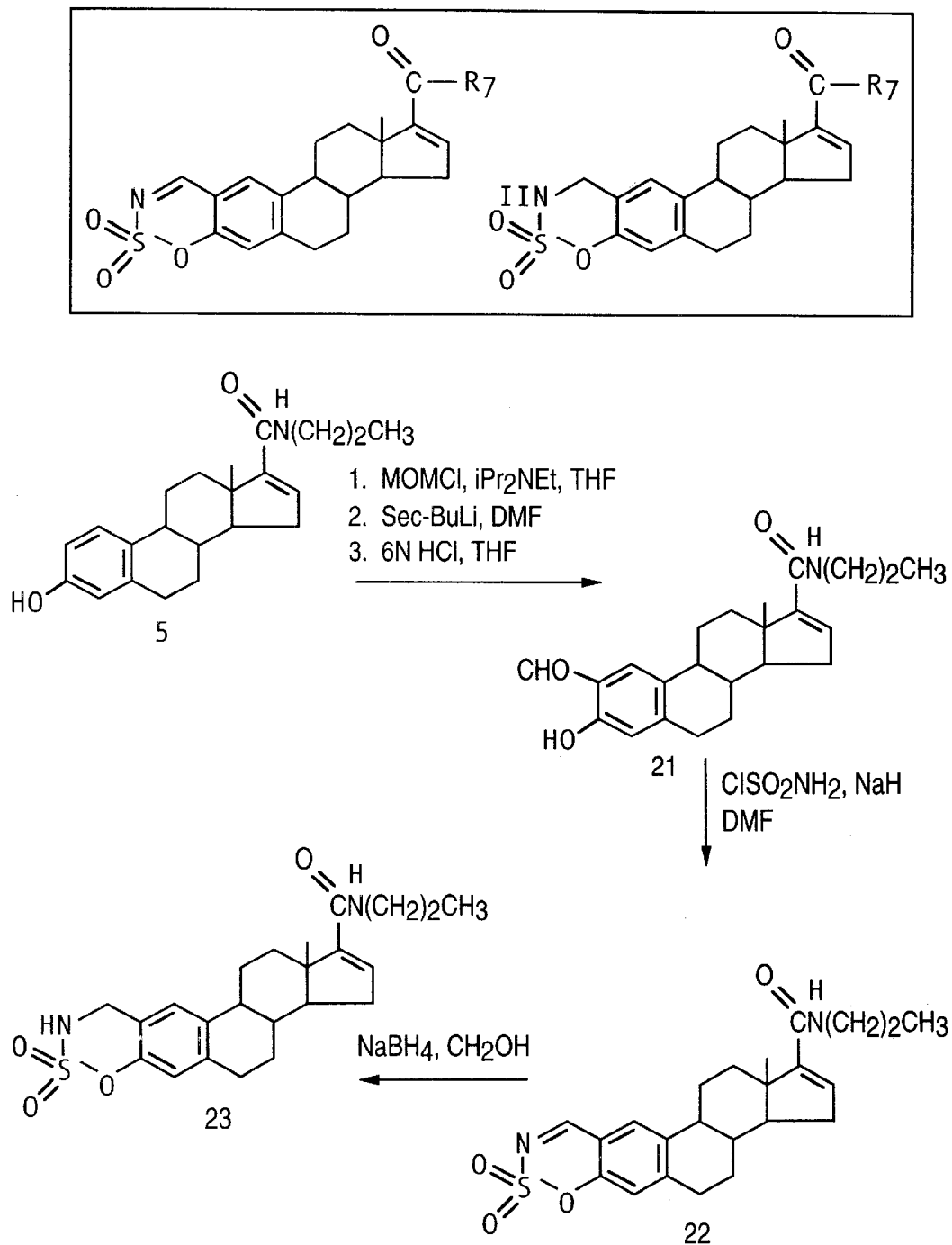
FIG. 9 illustrates a reaction scheme for preparing a compound of Class 10, according to the methods of Example 5.
Figure 10:
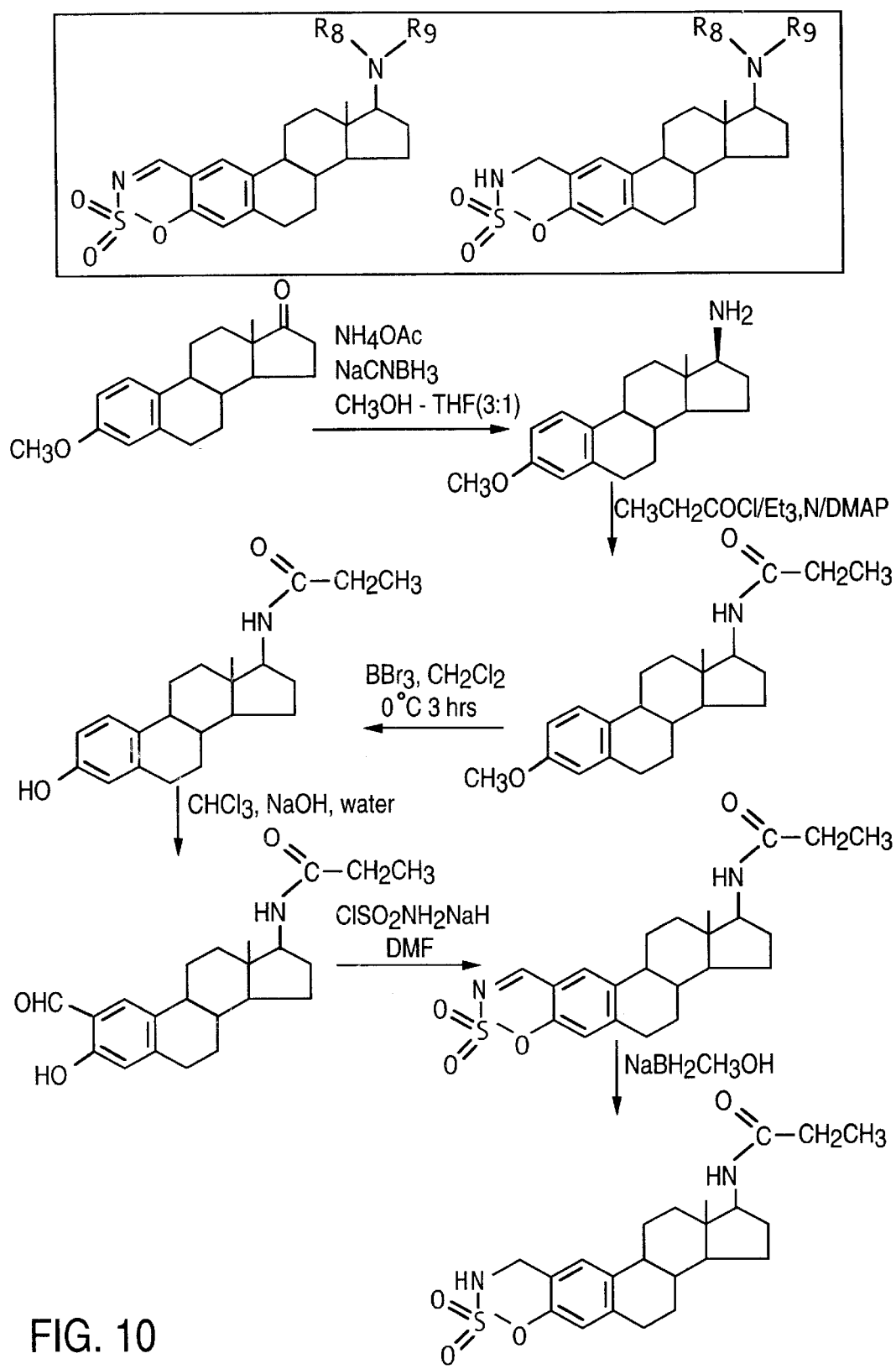
FIG. 10 illustrates a reaction scheme for preparing a compound of Class 12.

FIGS. 9 and 10 show synthesis schemes for preparation of compounds of Class 10 and Class 12. More specifically, FIG. 9 represents the synthesis of a Class 10 compound, which is represented by formula 3 wherein $R_3$ is equal to

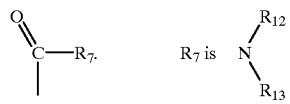

$R_{12}$ is hydrogen, and $R_{13}$ is a straight chain alkyl group having 3 carbons (propyl). FIG. 10 represents the synthesis of Class 12 compounds, represented by formula 3 above wherein $R_3$ is

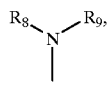

$R_8$ is hydrogen and $R_9$ is a straight chain alkanoyl group having 3 carbons. Again, by following the general synthesis schemes depicted in FIGS. 9 and 10, compounds generally represented by formula 3 above having a variety of substituents can be prepared by using the necessary compounds to obtain the desired sulfatase inhibitor.

Figure 11:
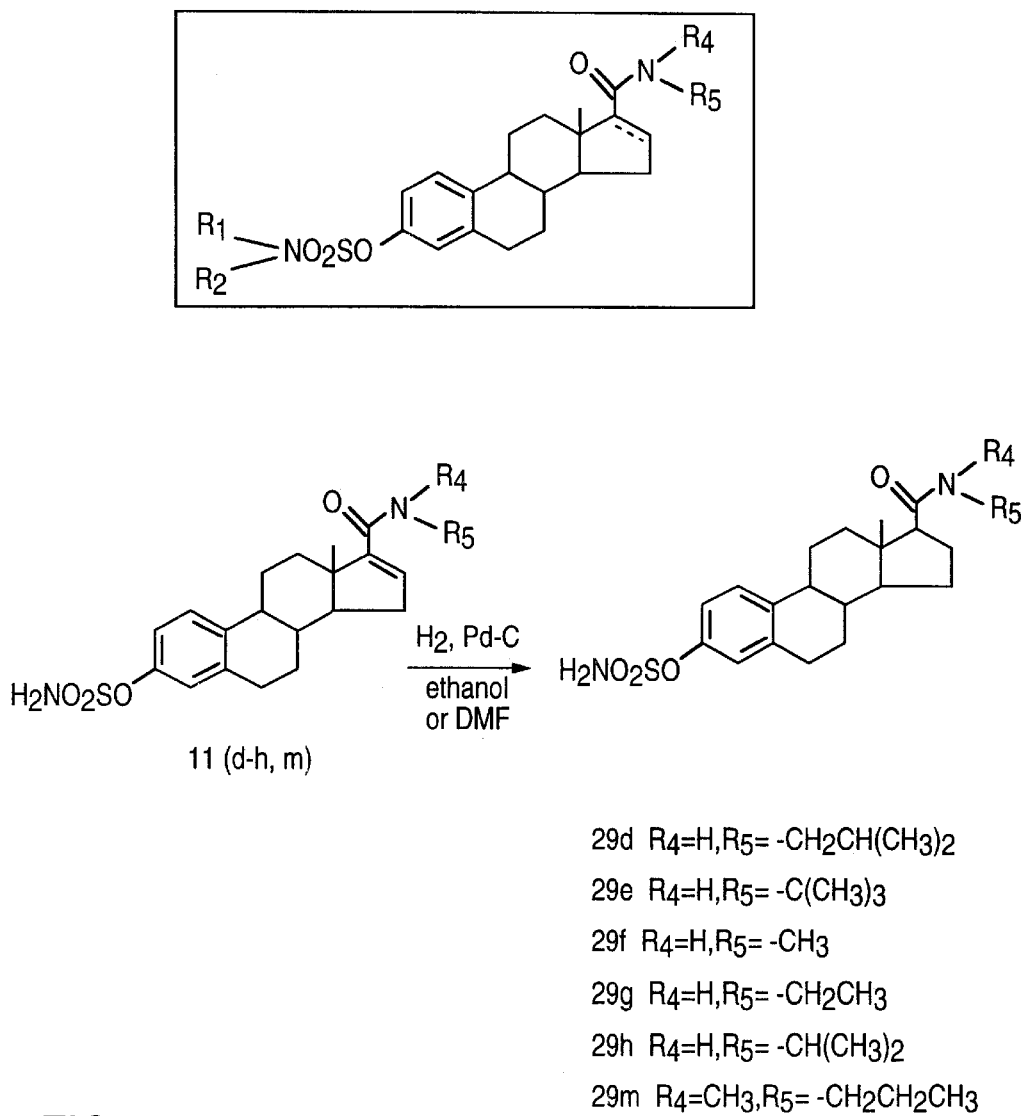
FIG. 11 illustrates a scheme for preparing compounds of Class 2, according to the methods of Example 4.

FIG. 11 shows a synthesis scheme for preparation of Class 2 compounds. The particular compounds synthesized in FIG. 11 are generally represented by formula 2 wherein $R_1$ and $R_2$ are both hydrogen, $R_3$ is

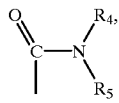

$R_4$ is hydrogen or methyl and $R_5$ is one of the "$R_5$" groups corresponding with compounds 29d, 29e, 29f, 29g, 29h and 29m in FIG. 11.

Figure 12:
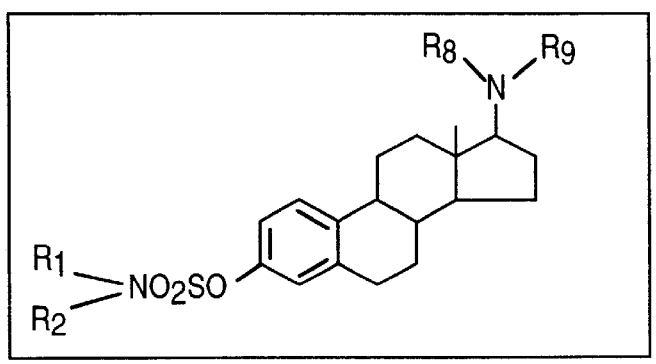
FIG. 12 illustrates a scheme for preparing a compound of Class 6, according to the methods of Example 6.
Figure 12:
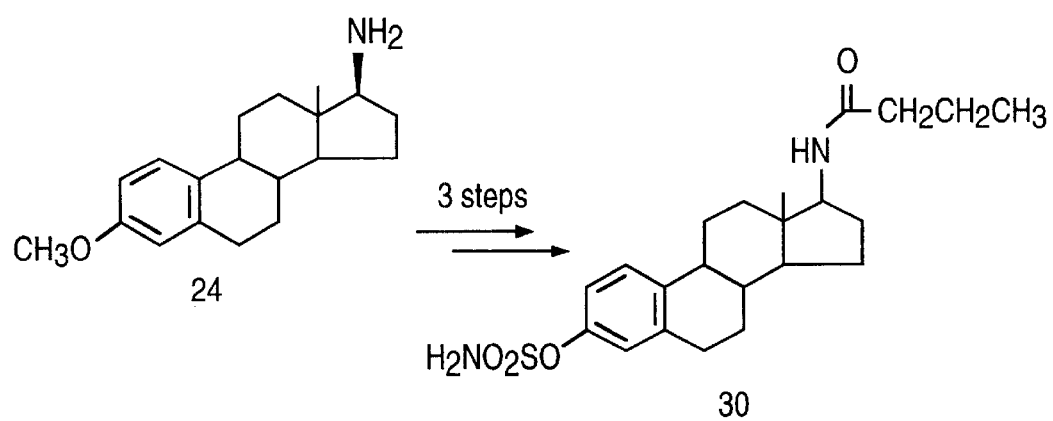

FIG. 12 shows a synthesis scheme for preparation of Class 6 compounds. The particular compound synthesized in FIG. 12 is generally represented by formula 2 wherein $R_1$ and $R_2$ are both hydrogen, $R_3$ is

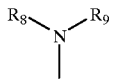

$R_8$ is hydrogen and $R_9$ is a butyryl group.

The present invention is further directed to methods for using the compounds described above to therapeutically and/or prophylactically treat a patient for an estrogen dependent illness. Such illnesses include, but are not limited to, breast cancer, vaginal cancer, endometrial cancer, ovarian cancer and endometriosis.

The methods of the present invention include the steps of: a) incorporating one or more of the compounds of the present invention in a suitable pharmaceutical carrier; and b) administering either a therapeutically effective dosage or a prophylactically effective dosage of the compounds incorporated in the carrier to a patient.

The term "suitable pharmaceutical carrier" refers to any carrier known in the pharmaceutical arts for administration of compounds to a patient. Any suitable pharmaceutical carrier can be used, so long as compatibility problems do not arise. A preferred pharmaceutical carrier is physiologic saline (0.9% sodium chloride), 95% dextrose in water.

Administration of an effective dosage or effective amount of the sulfatase inhibitor to a patient can be accomplished by parenteral injection, such as intravenously, intrathecally, intramuscularly or intra-arterially. The compounds can also be administered orally or transdermally, or by any other means known to those skilled in the art. Oral administration is preferred.

As used herein, the terms "effective amount" and "effective dosage" refer to that amount of one or more of the compounds disclosed herein required to achieve at least some level of enzyme inhibition in the patient. Typically, this will be an amount sufficient to impart a desired result or a desired treatment in a patient, such as reducing tumor size or lowering estrogen concentration. The term "therapeutically effective amount" refers to that amount of one or more of the compounds of the present invention required to therapeutically treat a patient. Such treatment is appropriate in patients having an estrogen-dependent illness. Similarly, the term "prophylactically effective amount" refers to that amount of one or more of the compounds of the present invention needed to prophylactically treat a patient. Such treatment is appropriate in patients who, for example, undergo surgery to remove cancerous growths; the compounds of the present invention would be administered to inhibit growth of any new tumor cells which appear. It will be appreciated that there is overlap between "therapeutic" and "prophylactic" treatment.

As will be appreciated by those skilled in the art, the dosage of compound given, the route of administration and the duration of therapy will be dependent upon the individual being treated, taking into consideration such factors as the particular estrogen dependent illness being treated, the body weight of the patient, other therapies being employed to treat the patient, and the condition, clinical response and tolerance of the patient. Dosage, administration, and duration of therapy can be determined by one skilled in the art upon evaluation of these and similar factors. A typical patient will be a post-menopausal female or pre-menopausal female who has been ovariectomized. Although the dosage and administration will vary from patient to patient, a typical dose will range between 0.005 mg and 2 mg of the present compounds per kg of body weight, and will be administered daily.

EXAMPLES

The following examples are intended to illustrate the invention and should not be construed as limiting the invention in any way.

For all of the examples, chemicals and silica gel were purchased from Aldrich Chemical Company (Milwaukee, Wis.). The chemicals were checked for purity by thin layer chromatography and NMR. Biochemicals, estrone and estrone sulfate were obtained from Sigma Chemical Company (St. Louis, Mo.). [6,7-$^3$H]Estrone sulfate was purchased from Dupont Company. Melting points were determined on a Thomas Hoover capillary melting point apparatus and were uncorrected. Proton NMR spectra were obtained with a Bruker WH-300 (300 MHz) spectrophotometer. Elemental analyses were performed by Atlantic Microlab Inc. is (Norcross, Ga.). Radioactive samples were analyzed with Packard Tri-Carb 4530 and Beckman LS-6500 Liquid Scintillation Counters. The liquid scintillation cocktail was Ecolume (ICN, Costa Mesa, Calif.), and Packard Utima Gold.

Example 1

Preparation of Class 1 Compounds

Reference numerals correspond with those shown in FIG. 3.

Synthesis of 3-Benzyloxyestrone (compound 2)

To a solution of estrone (compound 1) comprising 5 g (22 mmol) of compound 1 in acetone (150 ml) was added $K_2CO_3$ (4.56 g, 33 mmol) and benzyl bromide (3.9 ml, 33 mmol). The solution was refluxed for 2 days and the solution was evaporated to dryness and extracted with ethyl acetate. The ethyl acetate layer was dried ($Na_2SO_4$) and the solution was evaporated to dryness to give a yellowish solid. Excess benzyl bromide in the solid was washed out with petroleum ether to give a white solid (compound 2). The solid was used for the next step without further purification (~81% yield).

Synthesis of 3-Benzyloxy-17-(trifluoromethanesulfonyl) estra-1,3,5(10),16-tetraene (compound 3)

To a solution of compound 2, comprising 4.8 g (13 mmol) of compound 2 in $CH_2Cl_2$ (70 ml) was added 2,6-di-tert-butyl-4-methylpyridine (3 g, 14 mmol) and triflic anhydride (6 g, 27 mmol) at 0° C. The mixture was stirred for 5 hrs at room temperature and the mixture was filtered and the filtrate was washed with 10% sodium bicarbonate solution. The solution was then dried ($Na_2SO_4$), filtered and evaporated and chromatographed (petroleum ether:ethyl acetate, 2:1) to give a yellowish solid (5.2 g, 84.5%) (compound 3).

Synthesis of 3-Benzyloxy-17-(N-propylcarbamoyl)estra-1, 3,5(10),16-tetraene (compound 4)

A mixture of triflate compound 3 (1.4 g, 3.02 mmol), palladium (II) acetate (60 mg, 0.26 mmol), 1,3-Bis (diphenylphosphino)propane (dppp) (110 mg, 0.26 mmol), triethylamine (2 ml) and n-propylamine (7 ml) in dimethylformamide (DMF, 20 ml) was heated at 70° C. with carbon monoxide bubbled through for 5.5 hours. The reaction mixture was then diluted with ethyl acetate and washed with 10% aqueous hydrochloric acid (HCl), 10% aqueous sodium bicarbonate ($NaHCO_3$) and brine. The organic layer was dried with sodium sulfate ($Na_2SO_4$), concentrated and the residue was purified by silica gel chromatography and eluted with petroleum ether:ethyl acetate (EtOAc), (4:1), yielding the pure α,β-unsaturated amide (compound 4) (1.04 g, 80%). m.p. 136–138° C.; $^1H$ NMR (300 MHz, $CDCl_3$) δ 0.92 (t, 3H, $CH_2CH_3$), 0.99 (s, 3H, $CH_3$), 3.22–13.29 (q, 2H, $NHCH_2$), 5.0 (s, 2H, $CH_2Ph$), 5.63 (brs, 1H, NH), 6.30 (brs, 1H, 16-CH), 6.70 (d, 1H, ArH), 6.74–6.78 (dd, 1H, ArH), 7.17 (d, 1H, ArH), 7.29–7.42 (m, 5H, $CH_2Ph$).

Synthesis of 3-Hydroxy-17-(N-propylcarbamoyl)estra-1,3,5 (10),16-tetraene (compound 5)

Compound 4 (0.9 g, 2.09 mmol) was dissolved in chloroform (30 ml) and trimethylsilyl iodide (TMS-I, 0.9 ml, 6.28 mmol) was added in one portion to the reaction mixture at room temperature and the solution was stirred at room temperature for 3 hrs. Methanol (15 ml) was added to the solution to quench the reaction and the methanol was evaporated under reduced pressure. The remaining chloroform solution was washed with 10% sodium thiosulfate solution to neutralize the iodide and the solution was dried with sodium sulfate ($Na_2SO_4$). The solution was evaporated and chromatographed using gradient elution from plain $CH_2Cl_2$ to 10% ethyl acetate in $CH_2Cl_2$ yielding 605 mg of compound 5 (85.1% yield). m.p. 168.5–169° C.; $^1$HNMR (300 MHz, $CDCl_3$) δ 0.92 (t, 3H, $CH_2CH_3$), 0.99 (s, 3H, $CH_3$), 3.23–3.29 (q, 2H, $NHCH_2$), 4.66 (s, 1H, OH), 5.64 (brs, 1H, NH), 6.30 (brs, 1H, 16-CH), 6.55 (d, 1H, ArH), 6.59–6.63 (dd, 1H, ArH), 7.12 (d, 1H, ArH).

Synthesis of Compound 6

To a solution comprising 400 mg (0.93 mmol) of compound 5 and 2,6-di-tert-butyl-4-methylpyridine (DBMP) (0.6 g, 2.79 mmol) in $CH_2Cl_2$ (30 ml) was added sulfamoyl chloride (1 g, 8.6 mmol) portionwise with stirring at 0° C. The solution was stirred for 3.5 hrs at room temperature. The solution was washed with water until neutral, dried over $Na_2SO_4$, and evaporated under reduced pressure. The solid obtained was purified by chromatography ($CH_2Cl_2$:petroleum ether:ethyl acetate, 2:2:1) to give 404 mg of compound 6 (82.7%). m.p. 185.3–186° C.; $^1$HNMR (300 MHz, DMSO-$d_6$) δ 0.83 (t, 3H, $CH_2CH_3$), 0.91 (s, 3H, $CH_3$), 3.04 (t, 2H, $NHCH_2$), 6.34 (brs, 1H, 16-CH), 6.98 (d, 1H, ArH), 6.99–7.02 (dd, 1H, ArH), 7.32 (d, 1H, ArH), 7.74 (brs, 1H, $NHCH_2$), 7.89 (s, 2H, $NH_2$). Analysis calculated for $C_{22}H_{30}N_2O_4S$: C, 63.13; H, 7.22; N, 6.69. Found C, 63.36; H, 7.24; N, 6.63.

Synthesis of 17β-(N-Propylcarbamoyl)estra-1,3,5(10)-trien-3-yl Sulfamate (7)

A solution comprising 108 mg of compound 6 in 7 ml of ethanol was stirred over 15 mg of palladium (10 wt. % on activated carbon, 50% wet basis) under an atmosphere of hydrogen for 5 h. The catalyst was removed by filtration with diatomaceous earth and the filtrate was concentrated. The residue was purified by chromatography on silica gel (hexane:EtOAc, 1:1), yielding pure compound 7 (87 mg, 80%). $^1$H NMR (270 MHz, DMSO-$d_6$) δ 0.59 (s, 3H, $CH_3$), 0.84 (t, 3H, J=7.3 Hz, $CH_2CH_3$), 2.90 (dt, 2H, J=5.8, 7.3 Hz, $NHCH_2$), 3.07–3.20 (m, 1H, 17-CH), 6.95 (d, 1H, J=2.6 Hz, ArH), 7.00 (dd, 1H, J=2.6, 8.6 Hz, ArH), 7.33 (d, 1H, J=8.6 Hz, ArH), 7.46 (brt, 1H, J=5.8 Hz, $NHCH_2$), 7.83 (brs, 2H, $NH_2$).

Example 2

Preparation of Class 2 Compounds

Reference numerals correspond with those shown in FIGS. 4, 5 and 6.

Synthesis of 17-(N-Butylcarbamoyl)-3-(methoxy)estra-1,3, 5(10),16-tetraene (9a)

Oxalyl chloride 0.84 ml was added to a solution comprising 750 mg of compound 8 (described in *Tetrahedron Letters*, 26, 1109–1112, 1985) in 25 ml of anhydrous $CH_2Cl_2$ at 0° C. The solution was stirred at room temperature for 5 hours. After removal of the solvent and oxalyl chloride, 20 ml of anhydrous tetrahydrofuran (THF) was added to the reaction mixture. The solution of 4 ml was added to a solution comprising 0.19 ml of butylamine in 2 ml of THF at 0° C. and the solution was stirred for 2 hours. After evaporation of the solvent, 5 ml of water was added. The precipitate formed was filtered and triturated with 3 ml of isopropyl ether, yielding compound 9a (124 mg, 70%).

Synthesis of 17-(N-Butylcarbamoyl)-3-(hydroxy)estra-1,3,5 (10),16-tetraene (10a)

To a solution comprising 119 mg of compound 9a in 2 ml of anhydrous $CH_2Cl_2$ was added 0.64 ml of $BBr_3$ (1M solution in $CH_2Cl_2$) at -15° C. under nitrogen atmosphere. The reaction solution was stirred at room temperature for 1.3 hours and quenched by adding methanol and water at 0° C. The organic layer was separated and the aqueous layer was extracted with chloroform ($CHCl_3$). The combined organic layer was dried with $Na_2SO_4$ and concentrated in vacuo. The residue was triturated with 2.5 ml of EtOAc and 2.5 ml of hexane, yielding compound 10a (89 mg, 78%).

Synthesis of 17-(N-Butylcarbamoyl)estra-1,3,5(10),16-tetraen-3-yl Sulfamate (11a)

Sodium hydride (20 mg) was added to a solution comprising 73 mg of compound 10a in 2 ml of anhydrous DMF at 0° C. The solution was stirred for 25 minutes and 126 mg of chlorosulfonamide was added in one portion. The solution was then stirred at room temperature for 2 hours. Ice and saturated sodium bicarbonate solution was added to the reaction mixture. The precipitate formed was filtered and washed with water. The residue was purified by chromatography on silica gel (CHCl$_3$:methanol, 50:1), yielding compound 11a (85 mg, 96%). FAB-MS m/z 433 (M+H)$^+$; $^1$H NMR (270 MHz, DMSO-d$_6$) δ 0.88 (t, 3H, J=7.5 Hz, CH$_2$CH$_3$), 0.91 (s, 3H, CH$_3$), 3.08 (dt, 2H, J=5.6, 6.6 Hz, NHCH$_2$), 6.34 (s, 1H, 16-CH), 6.97 (s, 1H, ArH), 7.01 (dd, 1H, J=2.6, 8.6 Hz, ArH), 7.33 (d, 1H, J=8.6 Hz, ArH), 7.71 (t, 1H, J=5.6 Hz, NHCH$_2$), 7.88 (s, 2H, NH$_2$).

Synthesis of 17-(N-pentylcarbamoyl)estra-1,3,5(10),16-tetraen-3-yl Sulfamate (11b)

In similar manners to those described for the synthesis of sulfamate 11a, compound 11b was prepared from compound 8. FAB-MS m/z 447 (M+H)$^+$; $^1$H NMR (270 MHz, DMSO-d$_6$) δ 0.87 (t, 3H, J=6.7 Hz, CH$_2$CH$_3$), 0.91 (s, 3H, CH$_3$), 3.07 (dt, 2H, J=5.8, 6.6 Hz, NHCH$_2$), 6.34 (s, 1H, 16-CH), 6.97 (s, 1H, ArH), 7.01 (dd, 1H, J=2.3, 8.6 Hz, ArH), 7.33 (d, 1H, J=8.6 Hz, ArH), 7.71 (t, 1H, J=5.8 Hz, NHCH$_2$), 7.88 (s, 2H, NH$_2$).

Synthesis of 17-(N-Hexycarbamoyl)estra-1,3,5(10),16-tetraen-3-yl Sulfamate (11c)

In similar manners to those described for the synthesis of sulfamate 11a, compound 11c was prepared from compound 8. FAB-MS m/z 461 (M+H)$^+$; $^1$H NMR (270 MHz, DMSO-d$_6$) δ 0.86 (t, 3H, CH$_2$CH$_3$), 0.91 (s, 3H, CH$_3$), 3.07 (dt, 2H, NHCH$_2$), 6.34 (s, 1H, 16-CH), 6.97 (s, 1H, ArH), 7.01 (d, 1H, J=8.6 Hz, ArH), 7.33 (d, 1H, J=8.6 Hz, ArH), 7.71 (brt, 1H, NHCH$_2$), 7.88 (s, 2H, NH$_2$).

Synthesis of 17-(N-Isobutylcarbamoyl)estra-1,3,5(10),16-tetraen-3-yl Sulfamate (11d)

In similar manners to those described for the synthesis of sulfamate 11a, compound 11d was prepared from compound 8. FAB-MS m/z 433 (M+H)$^+$; $^1$H NMR (270 MHz, DMSO-d$_6$) δ 0.85 (d, 6H, J=6.9 Hz, CH(CH$_3$)$_2$), 0.92 (s, 3H, CH$_3$), 1.73 (m, 1H, CH(CH$_3$)$_2$), 2.78–3.00 (m, 2H, NHCH$_2$), 6.36 (s, 1H, 16-CH), 6.97 (d, 1H, J=2.3 Hz, ArH), 7.01 (dd, 1H, J=2.3, 8.6 Hz, ArH), 7.33 (d, 1H, J=8.6 Hz, ArH), 7.74 (t, 1H, J=6.3 Hz, NHCH$_2$), 7.88 (s, 2H, NH$_2$).

Synthesis of 17-(N-tert-Butylcarbamoyl)estra-1,3,5(10),16-tetraen-3-yl Sulfamate (11e)

In similar manners to those described for the synthesis of sulfamate 11a, compound 11e was prepared from compound 8. FAB-MS m/z 433 (M+H)$^+$; $^1$H NMR (270 MHz, DMSO-d$_6$) δ 0.92 (s, 3H, CH$_3$), 1.29 (s, 9H, C(CH$_3$)$_3$), 6.30 (s, 1H, 16-CH), 6.97 (d, 1H, J=2.3 Hz, ArH), 7.01 (m, 1H, ArH), 7.03 (s, 1H, NHC(CH$_3$)$_3$), 7.33 (d, 1H, J=8.6 Hz, ArH), 7.89 (s, 2H, NH$_2$).

Synthesis of 17-(N-Methylcarbamoyl)estra-1,3,5(10),16-tetraen-3-yl Sulfamate (11f)

In similar manners to those described for the synthesis of sulfamate 11a, compound 11f was prepared from compound 8. FAB-MS m/z 391 (M+H)$^+$; $^1$H NMR (270 MHz, DMSO-d$_6$) δ 0.91 (s, 3H, CH$_3$), 2.62 (d, 3H, J=4.6 Hz, NHCH$_3$), 6.35 (s, 1H, 16-CH), 6.97 (s, 1H, ArH), 7.02 (d, 1H, J=8.6 Hz, ArH), 7.33 (d, 1H, J=8.6 Hz, ArH), 7.69 (d, 1H, J=4.6 Hz, NHCH$_3$), 7.88 (s, 2H, NH$_2$).

Synthesis of 17-(N-Ethylcarbamoyl)estra-1,3,5(10),16-tetraen-3-yl Sulfamate (11g)

In similar manners to those described for the synthesis of sulfamate 11a, compound 11g was prepared from compound 8. FAB-MS m/z 405 (M+H)$^+$; $^1$H NMR (270 MHz, DMSO-d$_6$) δ 0.91 (s, 3H, CH$_3$), 1.03 (t, 3H, J=7.1 Hz, CH$_2$CH$_3$), 3.12 (m, 2H, CH$_2$CH$_3$), 6.36 (s, 1H, 16-CH), 6.97 (d, 1H, J=2.3 Hz, ArH), 7.01 (dd, 1H, J=2.3, 8.6 Hz, ArH), 7.33 (d, 1H, J=8.6 Hz, ArH), 7.75 (t, 1H, J=5.7 Hz, NHCH$_2$), 7.89 (s, 2H, NH$_2$).

Synthesis of 17-(N-Isopropylcarbamoyl)estra-1,3,5(10),16-tetraen-3-yl Sulfamate (11h)

In similar manners to those described for the synthesis of sulfamate 11a, compound 11h was prepared from compound 8. FAB-MS m/z 419 (M+H)$^+$; $^1$H NMR (270 MHz, DMSO-d$_6$) δ 0.91 (s, 3H, CH$_3$), 1.072 (d, 3H, J=5.6 Hz, CH(CH$_3$)$_2$), 1.074 (d, 3H, J=6.6 Hz, CH(CH$_3$)$_2$), 3.93 (m, 1H, CH(CH$_3$)$_2$), 6.36 (s, 1H, 16-CH), 6.97 (s, 1H, ArH), 7.01 (d, 1H, J=8.6 Hz, ArH), 7.33 (d, 1H, J=8.6 Hz, ArH), 7.52 (m, 1H, NHCH), 7.88 (s, 2H, NH$_2$).

Synthesis of 17-(N-Sec-Butylcarbamoyl)estra-1,3,5(10),16-tetraen-3-yl Sulfamate (11i)

In similar manners to those described for the synthesis of sulfamate 11a, compound 11i was prepared from compound 8. FAB-MS m/z 433 (M+H)$^+$; $^1$H NMR (270 MHz, DMSO-d$_6$) δ 0.82 (t, 3H, J=7.5 Hz, CH$_2$CH$_3$), 0.92 (s, 3H, CH$_3$), 1.04 (d, 3H, J=6.6 Hz, CHCH$_3$), 3.75 (m, 1H, CHCH$_3$), 6.34 (s, 1H, 16-CH), 6.98 (s, 1H, ArH), 7.02 (d, 1H, J=8.6 Hz, ArH), 7.33 (d, 1H, J=8.6 Hz, ArH), 7.44 (m, 1H, NHCH), 7.88 (s, 2H, NH$_2$).

Synthesis of 17-(N-tert-Amylcarbamoyl)estra-1,3,5(10),16-tetraen-3-yl Sulfamate (11j)

In similar manners to those described for the synthesis of sulfamate 11a, compound 11j was prepared from compound 8. FAB-MS m/z 447 (M+H)$^+$; $^1$H NMR (270 MHz, DMSO-d$_6$) δ 0.76 (t, 3H, J=7.4 Hz, CH$_2$CH$_3$), 0.92 (s, 3H, CH$_3$), 1.22 (s, 3H, C(CH$_3$)$_2$), 1.23 (s, 3H, C(CH$_3$)$_2$), 6.29 (s, 1H, 16-CH), 6.85 (m, 1H, 6.98 (s, 1H, ArH), 7.02 (d, 1H, J=8.6 Hz, ArH), 7.33 (d, 1H, J=8.6 Hz, ArH), 7.87 (s, 2H, NH$_2$).

Synthesis of 17-(N-isoamylcarbamoyl)estra-1,3,5(10),16-tetraen-3-yl Sulfamate (11k)

In similar manners to those described for the synthesis of sulfamate 11a, compound 11k was prepared from compound 8. FAB-MS m/z 447 (M+H)$^+$; $^1$H NMR (270 MHz, DMSO-d$_6$) δ 0.88 (d, 6H, J=6.6 Hz, CH(CH$_3$)$_2$), 0.91 (s, 3H, CH$_3$), 3.10 (m, 2H, NHCH$_2$), 6.33 (s, 1H, 16-CH), 6.97 (s, 1H, ArH), 7.01 (d, 1H, J=8.6 Hz, ArH), 7.33 (d, 1H, J=8.6 Hz, ArH), 7.69 (t, 1H, J=5.6 Hz, NHCH$_2$), 7.88 (s, 2H, NH$_2$).

Synthesis of 17-(N,N-Diethylcarbamoyl)estra-1,3,5(10),16-tetraen-3-yl Sulfamate (11l)

In similar manners to those described for the synthesis of sulfamate 11a, compound 11l was prepared from compound 8. TOF-MS m/z 433 (M+H)$^+$; $^1$H NMR (270 MHz, DMSO-d$_6$) δ 0.99 (s, 3H, CH$_3$), 1.05 (t, 6H, J=6.9 Hz, CH$_2$CH$_3$), 3.20–3.48 (m, 4H, CH$_2$CH$_3$), 5.76–5.82 (m, 1H, 16-CH), 6.96 (d, 1H, J=2.3 Hz, ArH), 7.01 (dd, 1H, J=2.3, 8.6 Hz, ArH), 7.31 (d, 1H, J=8.6 Hz, ArH), 7.84 (brs, 2H, NH$_2$).

Synthesis of 17-(N-methyl-N-propylcarbamoyl)estra-1,3,5(10),16-tetraen-3-yl Sulfamate (11m)

In similar manners to those described for the synthesis of sulfamate 11a, compound 11m was prepared from compound 8. TOF-MS m/z 433 (M+H)$^+$; $^1$H NMR (270 MHz, DMSO-d$_6$) δ 0.81 (t, 3H, J=7.6 Hz, CH$_2$CH$_3$), 0.99 (s, 3H, CH$_3$), 2.74–3.04 (m, 3H, NCH$_3$), 3.20–3.40 (m, 2H, NCH$_2$), 5.81 (brs, 1H, 16-CH), 6.96 (d, 1H, J=2.3 Hz, ArH), 7.00 (dd, 1H, J=2.3, 8.6 Hz, ArH), 7.31 (d, 1H, J=8.6 Hz, ArH), 7.84 (brs, 2H, NH$_2$).

Synthesis of 17-(N-ethoxycarbamoyl)estra-1,3,5(10),16-tetraen-3-yl Sulfamate (11n)

According to the four steps shown in FIG. 4, compound 1 in was prepared from compound 8a which was prepared from estrone acetate in accordance with a known method (for example, *Tetrahedron Letters* 26, 1109–1112, 1985). TOF-MS m/z 421 (M+H)$^+$; $^1$H NMR (270 MHz, DMSO-d$_6$)

δ 0.92 (s, 3H, CH$_3$), 1.15 (t, 3H, J=6.9 Hz, CH$_2$CH$_3$), 3.82 (q, 2H, J=7.2 Hz, CH$_2$CH$_3$), 6.29 (s, 1H, 16-CH), 6.98 (s, 1H, ArH), 7.02 (d, 1H, J=8.6 Hz, ArH), 7.33 (d, 1H, J=8.6 Hz, ArH), 7.88 (brs, 2H, NH$_2$), 10.93 (s, 1H, CONH).

Synthesis of 17-Carbamoylestra-1,3,5(10),16-tetraen-3-yl Sulfamate (11o)

Compound 11o was synthesized in a similar manner as 11a except that TMS-I was used in place of BBr$_3$. Compound 11o was prepared from compound 12. EI-MS m/z 376 M$^+$; $^1$H NMR (300 MHz, DMSO-d$_6$) δ 0.88 (s, 3H, CH$_3$), 6.44 (brs, 1H, 16-CH), 6.74 (brs, 2H, CONH$_2$), 6.97 (s, 1H, ArH), 7.01 (d, 1H, J=9 Hz, ArH), 7.32 (d, 1H, J=9 Hz, ArH), 7.89 (s, 2H, SO$_2$NH$_2$).

Synthesis of 17-(N,N-Dimethylcarbamoyl)estra-1,3,5(10), 16-tetraen-3-yl Sulfamate (11p)

Compound 11p was synthesized in a similar manner as 11a except that TMS-I was used in place of BBr$_3$. Compound 11p was prepared from compound 12. EI-MS m/z 404 M$^+$; $^1$H NMR (300 MHz, DMSO-d$_6$) δ 0.98 (s, 3H, CH$_3$), 2.93 (brs, 6H, N(CH$_3$)$_2$), 5.86 (s, 1H, 16-CH), 6.97 (s, 1H, ArH), 7.02 (d, 1H, J=9 Hz, ArH), 7.31 (d, 1H, J=9 Hz, ArH), 7.89 (s, 2H, SO$_2$NH$_2$).

Synthesis of 17-(N-methyl-N-methoxycarbamoyl)estra-1,3, 5(10),16-tetraen-3-yl-Sulfamate, (compound 11t)

Compound 11t was synthesized in a similar manner as 11a except that TMS-I was used in place of BBr$_3$. Compound 11t was prepared from compound 12. $^1$HNMR (250 MHz, DMSO-d$_6$) δ 0.80 (s, 3H, CH$_3$ ), 2.98 (s, 3H, NCH$_3$), 3.40 (s, 3H, OCH$_3$), 6.10 (s, 1H, 16-CH), 6.95 (s, 1H, ArH), 7.15 (dd, 1H, J=8.4 Hz, ArH), 7.30 (d, 1H, J=8.4 Hz, ArH), 7.95 (s, 2H, NH$_2$).

Synthesis of 17-(N, N-di-n-Propylcarbamoyl)estra-1,3,5 (10),16-tetraen-3-yl Sulfamate (compound 11q)

Compound 16q was obtained from compound 15 through carbonyl insertion-amidation; compound 11q was synthesized in a similar manner as 11a except that TMS-I was used in place of BBr$_3$. EI-MS m/z 460 M$^+$; $^1$H NMR (250 MHz, DMSO-d$_6$) δ 0.90 (t, 6H, CH$_2$CH$_3$), 1.09 (s, 3H, CH$_3$), 3.30–3.45 (m, 4H, NCH$_2$), 5.85 (s, 1H, 16-CH), 6.97 (s, 1H, ArH), 7.02 (d, 1H, J=8.6 Hz, ArH), 7.36 (d, 1H, J=8.6 Hz, ArH), 7.95 (s, 2H, SO$_2$NH$_2$).

Synthesis of 17-(N,N-Diisopropylcarbamoyl)estra-1,3,5 (10),1 6-tetraen-3-yl Sulfamate (compound 11r)

Compound 16r was obtained from compound 15 through carbonyl insertion-amidation; compound 11r was synthesized in a similar manner as 11a except that TMS-I was used in place of BBr$_3$. EI-MS m/z 460 M$^+$; $^1$H NMR (250 MHz, DMSO-d$_6$) δ 0.90 (s, 3H, CH$_3$), 1.30 (brs, 12H, CH(CH$_3$)$_2$), 3.90 (m, 2H, CH(CH$_3$)$_2$), 5.45 (s, 1H, 16CH), 6.75 (s, 1H, ArH), 6.85 (d, 1H, J=8.6 Hz, ArH), 7.10 (d, 1H, J=8.6 Hz, ArH), 7.70 (s, 2H, SO$_2$NH$_2$).

Synthesis of 17-(N-ethyl-N-Isopropylcarbamoyl)estra-1,3,5 (10),16-tetraen-3-yl Sulfamate (compound 11s)

Compound 16s was obtained from compound 15 through carbonyl insertion-amidation; compound 11s was synthesized in a similar manner as 11a except that TMS-I was used in place of BBr$_3$. EI-MS m/z 446 M$^+$; $^1$H NMR (250 MHz, DMSO-d$_6$) δ 1.20 (s, 3H, CH$_3$), 3.40 (m, 2H, CH$_2$CH$_3$), 4.45 (brs, 1H, CH(CH$_3$)$_2$), 5.90 (s, 1H, 16-CH), 7.15 (s, 1H, ArH), 7.30 (d, 1H, J=8.6 Hz, ArH), 7.50 (d, 1H, J=8.6 Hz, ArH), 8.05 (s, 2H, SO$_2$NH$_2$).

Example 3

Preparation of Class 3 Compounds

Reference numerals correspond with those shown in FIG. 7.

Synthesis of 3-Benzyloxy-17-(propylcarboxyl)estra-1,3,5 (10), 16-tetraene (compound 18)

A mixture of triflate (compound 15) (1.1 g, 2.37 mmol), palladium (II) acetate (45 mg, 0.20 mmol), 1,3-Bis (diphenylphosphino)propane (dppp) (66 mg, 0.16 mmol), and n-propanol (8 ml) in dimethylformamide (DMF, 10 ml) was heated at 60° C. with carbon monoxide bubbled through for 5.5 hours. The reaction mixture was then diluted with ethyl acetate and washed with water. The organic layer was dried with sodium sulfate (Na$_2$SO$_4$), concentrated and the residue was purified by silica gel chromatography and eluted with methylene chloride (CH$_2$Cl$_2$) yielding the pure α,β-unsaturated ester (compound 18) (875 mg, 89.1%). m.p. 84–85° C.; $^1$H NMR (300 MHz, CDCl$_3$) δ 0.97 (s, 3H, CH$_3$), 1.00 (t, 3H, J=7.5 Hz, CH$_3$), 4.13 (t, 2H, J=6.6 Hz, OCH$_2$), 5.05 (s, 2H, CH$_2$PH), 6.7–7.4 (m, 9H, 16-H and ArH).

Synthesis of 3-Hydroxy-17-(propylcarboxyl)estra-1,3,5 (10),16-tetraene (compound 19)

Compound 18 (780 mg, 1.81 mmol) was dissolved in CH$_2$Cl$_2$ (16 ml) and trimethylsilyl iodide (TMS-I, 0.9 ml, 6.28 mmol) was added in one portion to the reaction mixture at room temperature and the solution was stirred at room temperature for 15 min. Water was then added to the solution and the mixture was stirred for 30 min. The mixture was extracted with CH$_2$Cl$_2$ and the organic layer was separated and washed with 10% sodium thiosulfate solution to neutralize the iodide and the solution was dried with sodium sulfate (Na$_2$SO$_4$). The solution was evaporated and the residue was purified by silica gel chromatography and eluted with methylene chloride (CH$_2$Cl$_2$):ethyl acetate (EtOAc) (4:1) yielding compound 19 (590 mg, 95.7%) m.p. 139.7–140.7° C.

Synthesis of 17-(n-Propylcarboxyl)estra-1,3,5(10),16-tetraene (compound 20a)

To a solution of compound 19 comprising 250 mg (0.73 mmol) of compound 19 and 2,6-di-tert-butyl-4-methylpyridine (DBMP) (0.6 g, 3.23 mmol) in CH$_2$Cl$_2$ (30 ml) was added sulfamoyl chloride (1 g, 8.6 mmol) portionwise with stirring at 0° C. The solution was stirred for 3.5 hours at room temperature. The solution was washed with water until neutral, dried over Na$_2$SO$_4$, and evaporated under reduced pressure. The solid obtained was purified by chromatography (CH$_2$Cl$_2$/EtOAc, 4:1) to give 293 mg of 20 (95%). m.p. 113.9–115.2° C; $^1$HNMR (300 MHz, DMSO-d$_6$) δ 0.89 (s, 3H, CH$_3$), 0.92 (t, 3H, J=7.5 Hz, CH$_3$), 4.04 (t, 2H, J=6.3 Hz, OCH$_2$), 6.78 (brs, 1H, 16-CH), 6.98 (d, 1H, J=1.8 Hz, ArH), 7.02 (dd, 1H, J=1.8, 8.4 Hz, ArH), 7.33 (d, 1H, J=8.4 Hz, ArH), 7.91 (s, 2H, NH$_2$). Analysis calculated for C$_{22}$H$_{29}$NO$_5$S: C, 62.98; H, 6.97; N, 3.34. Found C, 62.86; H, 6.90; N, 3.32.

Synthesis of 17-(Ethylcarboxyl)estra-1,3,5(10),16-tetraen-3-yl-Sulfamate, (compound 20b)

Compound 20b was synthesized in a similar manner as compound 20a. $^1$H NMR (250 MHz, DMSO-d$_6$) δ 0.95 (s, 3H, 18-CH$_3$), 1.20 (t, 3H, J=7.2 Hz, CH$_3$), 4.10 (q, 2H, J=7.2 Hz, CH$_2$), 3.70 (s, 3H, CH$_3$), 6.70 (s, 1H, 16-CH), 6.92 (s, 1H, ArH), 6.98 (dd, 1H, J=8.4 Hz, ArH), 7.30 (d, 1H, J=8.4 Hz, ArH), 7.82 (s, 2H, NH$_2$).

Synthesis of 17-(Methylcarboxyl)estra-1,3,5(10),16-tetraen-3-yl-Sulfamate, (compound 20c)

Compound 20c was synthesized in a similar manner as compound 20a. $^1$H NMR (250 MHz, DMSO-d$_6$) δ 0.92 (s, 3H, CH₃), 3.70 (s, 3H, CH₃), 6.80 (s, 1H, 16-CH), 6.98 (s, 1H, ArH), 7.0 (dd, 1H, J=1.8, 8.4 Hz, ArH), 7.35 (d, 1H, J=8.4 Hz, ArH), 7.90 (s, 2H, NH₂).

Example 4

Preparation of Class 2 compounds

Reference numerals correspond with those shown in FIG. 11.

Synthesis of 17β-(N-Isobutylcarbamoyl)estra-1,3,5(10)-trien-3-yl Sulfamate (compound 29d)

In similar manners to those described for the synthesis of compound 7, compound 29d was prepared from compound 11d. TOF-MS m/z 435 (M+H)⁺; ¹H NMR (270 MHz, DMSO-d₆) δ 0.60 (s, 3H, CH₃), 0.84 (d, 6H, J=6.9 Hz, CH(CH₃)₂), 2.60–3.16 (m, 2H, NHCH₂), 6.95 (d, 1H, J=2.3 Hz, ArH), 7.00 (dd, 11H, J=2.3, 8.6 Hz, ArH), 7.34 (d, 1H, J=8.6 Hz, ArH), 7.49 (brt, 1H, J=5.6 Hz, NHCH₂) 7.84 (brs, 2H, NH₂).

Synthesis of 17β-(N-tert-Butylcarbamoyl)estra-1,3,5(10)-trien-3-yl Sulfamate (compound 29e)

In similar manners to those described for the synthesis of compound 7, compound 29e was prepared from compound 11e. FAB-MS m/z 435 (M+H)⁺; ¹H NMR (270 MHz, DMSO-d₆) δ 0.59 (s, 3H, CH₃), 1.26 (s, 9H, C(CH₃)₃), 6.89 (s, 1H, NH), 6.96 (d, 1H, J=2.3 Hz, ArH), 7.01 (dd, 1H, J=2.3, 8.6 Hz, ArH), 7.34 (d, 1H, J=8.6 Hz, ArH), 7.87 (s, 2H, NH₂).

Synthesis of 17β-(N-Methylcarbamoyl)estra-1,3,5(10)-trien-3-yl Sulfamate (compound 29f)

In similar manners to those described for the synthesis of compound 7, compound 29f was prepared from compound 11f. FAB-MS m/z 393 (M+H)⁺; ¹H NMR (270 MHz, DMSO-d₆) δ 0.60 (s, 3H, CH₃), 2.59 (d, 3H, J=3.6 Hz, NHCH₃), 6.96 (d, 1H, J=2.3 Hz, ArH), 7.01 (dd, 1H, J=2.3, 8.6 Hz, ArH), 7.34 (d, 1H, J=8.6 Hz, ArH), 7.29 (m, 1H, NHCH₃), 7.87 (s, 2H, NH₂).

Synthesis of 17β-(N-Ethylcarbamoyl)estra-1,3,5(10)-trien-3-yl Sulfamate (compound 29g)

In similar manners to those described for the synthesis of compound 7, compound 29g was prepared from compound 11g. FAB-MS m/z 407 (M+H)⁺; ¹H NMR (270 MHz, DMSO-d₆) δ 0.60 (s, 3H, CH₃), 1.01 (t, 3H, J=7.3 Hz, CH₂CH₃), 3.02 (m 1H, CH₂CH₃), 3.16 (m, 1H, CH₂CH₃), 6.96 (d, 1H, J=2.0 Hz, ArH), 7.01 (d,1H, J=8.6 Hz, ArH), 7.34 (d, 1H, J=8.6 Hz, ArH), 7.47 (t, 1H, J=5.6 Hz, NHCH₂), 7.87 (s, 2H, NH₂).

Synthesis of 17β-(N-Isopropylcarbamoyl)estra-1,3,5(10)-trien-3-yl Sulfamate (compound 29h)

In similar manners to those described for the synthesis of compound 7, compound 29h was prepared from compound 11h. TOF-MS m/z 421 (M+H)⁺; ¹H NMR (270 MHz, DMSO-d₆) δ 0.58 (s, 3H, CH₃), 1.00–1.10 (m, 6H, CH(CH₃)₂), 3.38–3.50 (m, 1H, CH(CH₃)₂), 6.95 (d, 1H, J=2.3 Hz, ArH), 7.00 (dd, 1H, J=2.3, 8.6 Hz, ArH), 7.27 (d, 1H, J=7.9 Hz, NHCH), 7.33 (d, 1H, J=8.6 Hz, ArH), 7.85 (brs, 2H, NH₂).

Synthesis of 17β-(N-Methyl-N-propylcarbamoyl)estra-1,3,5(10)-trien-3-yl Sulfamate (compound 29m)

In similar manners to those described for the synthesis of compound 7, compound 29m was prepared from compound 11m. TOF-MS m/z 435 (M+H)⁺; ¹H NMR (270 MHz, DMSO-d₆) δ 0.60–0.68 (m, 3H, CH₃), 0.76–0.88 (m, 3H, CH₂CH₃), 2.70–3.70 (m, 5H, N(CH₃)CH₂), 6.95 (d, 1H, J=2.6 Hz, ArH), 7.00 (dd, 1H, J=2.6, 8.6 Hz, ArH), 7.32 (d, 1H, J=8.6 Hz, ArH), 7.83 (brs, 2H, NH₂).

Example 5

Preparation of Class 10 Compounds

Reference numerals correspond with those shown in FIG. 9.

Synthesis of 17-(N-n-Propylcarbamoyl)-estra-1,3,5(10),16-tetraen-[3,2,e]-1'2'3'-oxathiazine-2,2'-dioxide (compound 22)

To a solution of compound 21 (0.37g, 1.0 mmol) in DMF (10 ml) was added sodium hydride (0.115 g, 5 mmol) at 0° C. The reaction mixture was stirred for 20 minutes and chlorosulfonamide (0.73 g, 5 mmol) was added. The solution was stirred for an additional 6 hrs. The reaction mixture was poured into ice cold saturated NH₄Cl solution and then extracted with EtOAc. The organic layer was separated, washed with water, brine and dried (Na₂SO₄). The solvent was evaporated under reduced pressure and the residue was purified by silica gel chromatography (CH₂Cl₂; EtOAc, 15:1). FAB-MS m/z 428 (M+H)⁺; NMR (250 MHz, DMSO-d₆) δ 0.65 (t, 3H, CH₂CH₃), 0.70 (s, 3H, CH₃), 6.15 (s, 1H, 16-CH), 7.01 (s, 1H, ArH), 7.55 (m, 1H, NH), 7.70 (s, 1H, ArH), 8.90 (s, 1H —CH=N—).

Synthesis of 17-(N-n-Propylcarbamoyl)-estra-1,3,5(10),16-tetraen-[3,2,e]-3'4'-dihydro-1'2'3'-oxathiazine-2,2'-dioxide (compound 23)

To a solution of compound 22 (0.428 g, 1 mmol) in methanol (4 ml) was added NaBH₄ (0.037 g, 0.96 mmol) at 0° C. The reaction was stirred at 0° C. for 1 hr and the mixture was poured into saturated NH₄Cl and extracted with EtOAc. The organic layer was separated, washed with water, brine and died (Na₂SO₄) and the solvent was evaporated under reduced pressure. The residue was purified by silica gel chromatography (EtOAc:Pet ether, 1:1). FAB-MS m/z 430 (M+H)⁺; ¹H NMR (250 MHz, DMSO-d₆) δ 0.65 (t, 3H, CH₂CH₃), 0.75 (s, 3H, CH₃), 4.30 (s, 2H, CH₂NHSO₂), 6.20 (s, 1H, 16-CH), 6.55 (s, 1H, ArH), 7.05 (s, 1H, ArH), 7.60 (m, 1H, amide NH), 8.25 (m, 1H, CH₂NHSO₂).

Example 6

Preparation of Class 6 compounds

Reference numerals correspond with those shown in FIG. 12.

Synthesis of 17β-(Butyrylamino)estra-1,3,5(10)-trien-3-yl Sulfamate (compound 30)

Compound 30 was prepared from compound 24 in three steps (amidation, deprotection and sulfamoylation) according to the method taught by Li, et al. *Steroids*, 63:425–32 (1998). FAB-MS m/z 421 (M+H)⁺; ¹H NMR (270 MHz, DMSO-d₆) δ 0.65 (s, 3H, CH₃), 0.86 (t, 3H, J=7.6 Hz, CH₂CH₃), 2.07 (m, 2H, COCH₂), 3.81 (m, 1H, 17-CH), 6.96 (d, 1H, J=2.3 Hz, ArH), 7.00 (d, 1H, J=8.6 Hz, ArH), 7.32 (d, 1H, J=8.6 Hz, ArH), 7.48 (d, 1H, J=8.9 Hz, NHCO), 7.87 (s, 2H, NH₂).

Example 7

The compounds prepared according to the methods of the above Examples were tested for biological activity in inhibiting sulfatase activity using an in vitro conversion assay procedure. The specific compounds tested are shown in Table 2, below. As will be appreciated by those skilled in the art, this assay is based on inhibition of the conversion of ³H-estrone sulfate to ³H-estrone by the enzyme estrone sulfatase. The final volume of the enzyme assay was 0.15 ml. [6.7-³H] estrone sulfate (final concentration 3.3 nmole/L; 300,000 dpm/tube); an inhibitor at various concentrations in DMSO and recombinant human estrone sulfatase (33 ng/tube) in phosphate buffered saline, containing 0.25 M sucrose and 0.04 M nicotinamide, pH 7, were added to a 1.5 ml microtube. Recombinant human estrone sulfatase was partially purified from Chinese Hamster Ovary (CHO) cells in which human estrone sulfatase cDNA was transfected. The assay began by the addition of the substrate estrone sulfate. After 60 minutes of incubation at 37° C., 0.5 ml of toluene were added to quench the assay. Control samples with no inhibitor were incubated simultaneously. Blank samples were obtained by incubating without estrone sulfatase. The quenched samples were vortexed for 30 seconds and centrifuged (9,000 rpm for 5 minutes). Two hundred and fifty microliters of toluene were obtained from each quenched sample to determine the amount of product formation. Product formation for samples containing an inhibitor was compared to that of control samples (without inhibitors) run simultaneously. This was reported as percent inhibition of control sample which equals $$100 \times \frac{\text{Product formation for sample containing inhibitor}}{\text{Product formation for sample with no inhibitor (control)}}$$

Each compound was tested over a range of concentrations (0.025 to 2.5 nM) for determination of dose-responsiveness and for calculation of $IC_{50}$ values. Each concentration was tested in duplicate in three separate experiments. Both compounds showed dose-dependent inhibition of estrone sulfatase activity as determined by the in vitro conversion assay. The $IC_{50}$ values, representing the concentration that resulted in 50% inhibition of estrone sulfatase activity in this assay, are shown in Table 2. The $IC_{50}$ values were determined by performing linear regression analysis of percent of control versus concentration (log10); the resulting equation was then used to determine the concentration that resulted in 50% inhibition.

TABLE 2

| $R_3$ | $IC_{50}$(nmol/L) |
|---|---|
| O=C(H)NCH₃ | 12 |
| O=C(H)NCH₂CH₃ | 14 |
| O=C(H)N(CH₂)₂CH₃ | 5 |

TABLE 2-continued

| $R_3$ | $IC_{50}$(nmol/L) |
|---|---|
| O=C(OCH₃)NCH₃ | 12 |
| O=C(O)COCH₃ | 12 |
| O=C(O)COCH₂CH₃ | 12 |
| O=C(O)COCH₂CH₂CH₃ | 13 |
| COOH | 50 |
| O=C(H)NCH₂CH(CH₃)₂ | 10 |
| O=C(H)NC(CH₃)₃ | 12 |
| O=C(H)NCH(CH₃)₂ | 3.2 |
| O=C(H)NCH(CH₃)CH₂CH₃ | 3.5 |
| O=C(CH₂CH₃)NCH₂CH₃ | 3.6 |
| O=C(CH₃)NCH₂CH₂CH₃ | 2.5 |

TABLE 2-continued

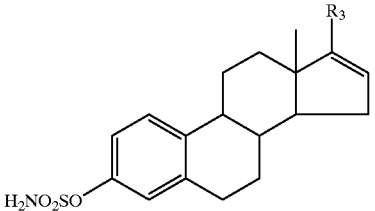

| $R_3$ | $IC_{50}(nmol/L)$ |
|---|---|
| 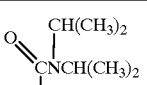 | 4.8 |

Example 8

Compounds 7, 29d, 29h and 29m were tested in the manner described for Example 6. Results are presented in Table 3.

TABLE 3

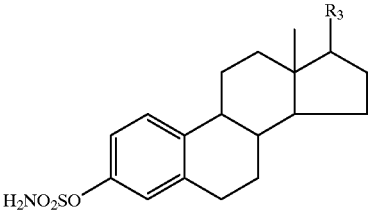

| $R_3$ | $IC_{50}(nmol/L)$ |
|---|---|
| 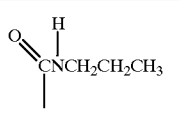 | 19 |
| 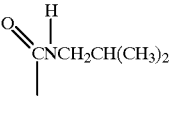 | 6.5 |
| 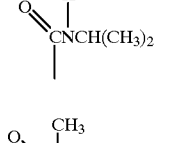 | 17 |
| 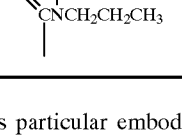 | 5.5 |

Whereas particular embodiments of this invention have been described above for purposes of illustration, it will be evident to those skilled in the art that numerous variations of the details of the present invention may be made without departing from the invention as defined in the appended claims.

What is claimed is:

1. A compound having the formula:

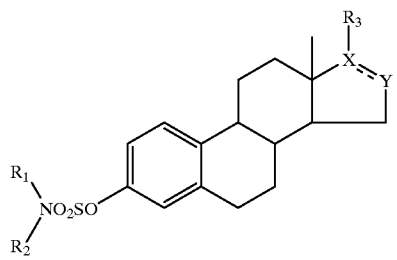

wherein X and Y are both carbons and the bond between X and Y is either single or double;

wherein $R_1$ and $R_2$ are independently selected from hydrogen and a lower alkyl group having one to six carbons; and $R_3$ is:

$R_4$ and $R_5$ are independently selected from straight or branched chain alkyl groups having one to fourteen carbons, and straight or branched chain alkoxy groups having one to six carbons.

2. The compound of claim 1, wherein $R_1$ and $R_2$ are both hydrogen and the bond between X and Y is double.

3. The compound of claim 2, wherein $R_5$ is selected from the group consisting of methyl, ethyl, propyl, isopropyl, isobutyl, tert-butyl, sec-butyl, isopentyl, hexyl and ethoxy groups.

4. The compound of claim 2, wherein $R_4$ is an ethyl group and $R_5$ is selected from the group consisting of ethyl and isopropyl groups.

5. The compound of claim 2, wherein $R_4$ is methyl and $R_5$ is propyl.

6. The compound of claim 2, wherein $R_4$ and $R_5$ are both methyl groups, both propyl groups or both isopropyl groups.

7. The compound of claim 1, wherein $R_1$ and $R_2$ are both hydrogen and the bond between X and Y is single.

8. The compound of claim 7, wherein $R_5$ is selected from the group consisting of methyl, ethyl, propyl, isopropyl, isobutyl and tert-butyl groups.

9. The compound of claim 7, wherein $R_4$ is a methyl group and $R_5$ is a propyl group.

* * * * *

UNITED STATES PATENT AND TRADEMARK OFFICE
CERTIFICATE OF CORRECTION

PATENT NO. : 6,376,687 B1  Page 1 of 1
DATED : April 23, 2002
INVENTOR(S) : Pui-Kai Li et al.

It is certified that error appears in the above-identified patent and that said Letters Patent is hereby corrected as shown below:

<u>Title page,</u>
Item [56], OTHER PUBLICATIONS, "*Int. H. Cancer,*" should read -- *Int. J. Cancer* --.

<u>Column 1,</u>
Line 45, ""!In vivo" should read -- In vivo --.

<u>Column 7,</u>
Formula mid-page, remove the "," after "N" in formula, insert the -- , -- after "$R_{13}$," last line of the formula.

<u>Column 8,</u>
Line 60, "Class 3" should read -- Class 4 --.

<u>Column 9,</u>
Line 9, remove the "," after "$R_7$," place the -- , -- after "$R_{13}$".
Line 37, insert a -- , -- after "$R_5$".

<u>Column 11,</u>
Line 45, "13.29" should read -- 3.29 --.

<u>Column 14,</u>
Line 64, "1" should read -- 11n --.

<u>Column 17,</u>
Line 25, "lie" should read -- 11e --.

Signed and Sealed this

Eighteenth Day of March, 2003

JAMES E. ROGAN
*Director of the United States Patent and Trademark Office*